United States Patent [19]

Kearney et al.

[11] Patent Number: 5,589,335

[45] Date of Patent: Dec. 31, 1996

[54] HYBRIDIZATION PROMOTION REAGENTS

[75] Inventors: Kevin R. Kearney, Worcester, Mass.; Mark L. Collins, Walnut Creek, Calif.; John K. Eldredge, Brewster, Mass.; David V. Morrissey, Middletown, Conn.

[73] Assignee: Amoco Corporation, Chicago, Ill.

[21] Appl. No.: 290,001

[22] Filed: Aug. 11, 1994

Related U.S. Application Data

[63] Continuation-in-part of Ser. No. 93,406, Jul. 19, 1993, abandoned, which is a continuation of Ser. No. 821,334, Jan. 13, 1992, abandoned, which is a continuation of Ser. No. 333,656, Apr. 5, 1989, abandoned.

[51] Int. Cl.$^6$ .................................................. C12Q 1/68
[52] U.S. Cl. .................. 435/6; 935/78; 935/79; 435/967
[58] Field of Search ................ 435/6, 967; 935/78, 935/79

[56] References Cited

FOREIGN PATENT DOCUMENTS 0229442  7/1987  European Pat. Off. .
8706621  5/1986  WIPO .

OTHER PUBLICATIONS

Thompson et al., Anal. Biochem. 163(2):281–291, 1987.
Orosy, DNA Iodination, Provirus Isolation, Excluded Volume and Electrostatic Effects on DNA Renaturation Rate, Dissertation Information Service, 1975, pp. 1–4 and 167–176.
Melchior et al., Proc. Natl Acad Sci. 70(2):298–02, 1973.
Douglass et al., Methods of Enzymology 124:309–318, 1986.
Hames et al, Nucleic Acid Hybridization, IRL Press, Wash., D.C., 1985, p. 6.
Rawn, Biochemistry, Harper & Row, N.Y., N.Y. 1983, p. 1055.
Wood et al., Proc. Natl.Acad.Sci. 82:1585–88, 1985.
DiLella et al, Method in Enzymology 152:447–451.
Devlin et al., DNA 7(7):499–05, 1988.

*Primary Examiner*—Stephanie W. Zitomer
*Assistant Examiner*—Scott W. Houtteman
*Attorney, Agent, or Firm*—Norval B. Galloway

[57] ABSTRACT

Novel reagents are provided along with methods for their use in nucleic acid hybridization assays for detecting target nucleic acids in samples. The most preferred reagent is a mixture of guanidinium thiocyanate and tetramethylammonium:Trifluoracetate and possesses many properties for facilitating hybridization between target nucleic acid and nucleic acid probes capable of binding thereto and surprisingly results in the phenomenon of superstoichiometric labeling.

12 Claims, 3 Drawing Sheets

HYBRIDIZATION PROMOTION REAGENTS

This is a continuation in part of application Ser. No. 08/093,406, filed Jul. 19, 1993, now abandoned, which is a continuation of Ser. No. 07/821,334, now abandoned which is a continuation of application Ser. No. 07/333,656, filed Apr. 5, 1989, now abandoned.

FIELD OF THE INVENTION

This invention pertains to the field of nucleic acid hybridization assays and more specifically involves novel reagents for conducting and promoting hybridization of nucleic acid probes with target nucleic acids from a food or clinical sample.

BACKGROUND OF THE INVENTION

Specific association of complementary nucleic acid takes place in a reaction commonly referred to as hybridization. This technique has made possible the sensitive and specific detection, and the isolation, of nucleic acid sequences. In this technique, one prepares a nucleic acid probe which is complementary to a target nucleic acid, and then by selecting the appropriate conditions causes these two entities to bind to each other to form a hybrid. By judiciously choosing the reaction conditions, e.g. temperature, ionic strength and the like, one prevents non-complementary nucleic acids from hybridizing. Hybrids can be formed on a solid support, in tissue sections or in solution. In the last case they are subsequently separated from a mixture of nucleic acids by one of a variety of methods and immobilized on a solid support. The formation of hybrids can be followed if a "reporter" probe contains a detectable element, such as a radioactive atom, an enzyme with detectable activity, a hapten to which an enzyme-conjugated antibody can bind, or generally any entity to which an enzyme-conjugated ligand can bind.

Since its discovery, nucleic acid hybridization has been used extensively as a research tool. More recently, it has been put to use as a medical diagnostic technique, as a method for testing food for the presence of pathogens, in agriculture, etc. In these fields, hybridization is in its infancy: there is an ongoing need to develop improved techniques, to make the assay methods more sensitive, more specific, faster and easier to use. It is one aspect of the present invention to provide an improved reagent for use in hybridization assays.

Most hybridization assays are done overnight with targets immobilized on filters (Nygaard, A. P. and Hall, B. D. (1963) Biochem. Biophys. Res. Commun. 12, 98–104; Gillespie, D. and Spiegelman, S. (1965) J. Molec. Biol. 12, 829–842; Southern, E. M. (1975) J. Molec. Biol. 98, 503–517). Though these techniques have been extremely useful for research purposes and have made possible a variety of significant discoveries, a suitable clinical assay must be much more rapid (with results available within an hour or two of specimen collection), as well as being simpler (filter immobilization is not trivial, especially with clinical samples) and more sensitive.

The nucleic acids in a hybridization reaction generally have to be highly purified prior to immobilization, especially when non-radioactive detection is used (Ruth, J. L. and Bryan, R. N. (1984) Fed. Proc. 43, 2048; Kuritza, A. P., Getty, C. E., Shaughnessy, P., Hesse, R. and Salyers, A. A. (1986) J. Clin. Microbiol. 23, 343–349; Zwadyk, P., Cooksey, R. C. and Thornsberry, C. (1986) Curr. Microbiol. 14, 95–100). While this is less of a major problem in a research setting, this is unacceptable in a clinical situation because nucleic acid purification can be a multi-step, time-consuming process, where an assay must be rapid and simple.

It is another aspect of the present invention to provide a clinical assay incorporating a rapid and simplified sample preparation step along with reagents suitable therefor. Gillespie (International Application No. WO 87/06621, dated 5 Nov. 1987) has described a method of carrying out nucleic acid hybridizations which does not require prior purification and/or immobilization of solubilized target nucleic acids. In this method, guanidinium thiocyanate serves both to solubilize a target nucleic acid and to permit hybridization. While this technique overcame some of the problems associated with the development of a rapid, simple and versatile nucleic acid hybridization assay appropriate for use in a clinical setting, the technique shared many of the same limitations inherent in other hybridization procedures. For example, there remained an absolute limit on the extent of nucleic acid labeling by hybridization: at most, one complementary reporter probe can bind to each accessible binding site on the target molecule. Furthermore, as with other methods, hybridization rates and optimal hybridization temperatures depend on the target sequence's (G+C) content, a parameter which can vary considerably (discussed in detail below).

It is still another aspect of the present invention to provide reagents which do not depend upon the G+C content of target sequences as do conventional reagents.

When highly impure samples have been immobilized on filters, detection has been limited for the most part to radioactive methods (Bresser, J., Doering, J. and Gillespie, D. (1983) DNA 2, 243–254; Fitts, R. (1985) Food Technology 39, 95–102). This presents a significant problem for a clinical laboratory, since many are not licensed to work with radioactive materials, some personnel have little or no experience working with radioactive materials, work with radioactive materials involves some health risk, and radioactivity decays with time (in the case of certain isotopes, quite rapidly) and can cause radiolysis of probes, thus limiting the usable lifetimes of these materials and reducing the feasibility of a clinical assay employing the materials. Non-radioactive detection methods have been developed (for example, see Leafy, J. J., Brigati, D. J. and Ward, D. C. (1983) Proc. Natl. Acad. Sci. USA 80, 4045–4049), but their sensitivity has not matched that of the radioactive methods except where the target was highly purified prior to hybridization and detection.

'Sandwich hybridization' assays were developed (Dunn, A. R. and Hassell, J. A. (1977) Cell 12, 23–36; Ranki, M., Palva, A., Virtanen, M., Laaksonen, M. and Soderlund, H. (1983) Gene 21, 77–85; Virtanen, M., Palva, A., Laaksonen, M., Halonen, P., Soderlund, H. and Ranki, M. (1983) Lancet 1, 383–393) in an attempt to overcome some of the limitations of conventional hybridization techniques. The target nucleic acid is 'sandwiched' between a capture probe immobilized on a solid support and a labeled probe which is complexed with the target in solution. Though the 'sandwich' technique represented an improvement in some aspects of nucleic acid hybridizations, the procedure still retained certain weaknesses, notably its slowness, its clinically insufficient sensitivity and its seemingly inherent background problems thus lowering sensitivity and specificity.

Various techniques have been developed to accelerate the hybridization process. For example the two-phase phenol/aqueous emulsion procedure (Kohne, D. E., Levinson, S. A., and Byers, M. J. (1977), Biochemistry 16, 5329) has been reported to result in reaction rates over 100 times faster than reference rates. Deficiencies of this method, however, are that it fails to boost reaction rates to the same extent when RNA is involved, that it requires that the reaction vessel be agitated during the hybridization process, and that it involves a chemical (phenol) associated with certain health risks.

It is still another aspect of the present invention to provide reagents which are effective in improving RNA hybridization rates.

It is still yet another aspect of the present invention to provide assays which overcome some of the deficiencies of conventional assays.

It is yet still another aspect of the present invention to provide reagents which do not pose the health risks associated with phenol.

Another technique reported to accelerate hybridization reactions is to add to a reaction mixture volume exclusion reagents, such as polyethylene glycol (Renz and Kurz (1984), Nucl. Acids Res., 12, 3435–3444), dextran or dextran sulfate (Wetmur, J. G. (1975), Biopolymers 14, 2517–2524; Wahl, G. M., Stern, M., and Stark, G. R. (1979), Proc. Natl. Acad. Sci. USA 76, 3683–3687; Wahl, G. M. and Stark, G. R., U.S. Pat. No. 4,302,204, Nov. 24, 1981), polyacrylate or polymethacrylate (Boguslawski, S. J. and Anderson, L. H. D., U.S. Pat. No. 4,689,294, Aug. 25, 1987). Though these methods accelerate hybridization when a target is immobilized the acceleration is less dramatic in solution hybridizations. Furthermore, while these techniques increase hybridization rates, they do not raise final hybridization levels.

It is still further an aspect of the present invention to provide reagents which increase hybridization rates in solution hybridization.

It is another still further aspect of the present invention to provide reagents which raise final hybridization levels.

Kohne and Kacian (European Patent Application number 86304429.3) have also reported a method of accelerating nucleic acid hybridization using different agents that also precipitate nucleic acids. In their application, the claims are limited to increased rates of nucleic acid reassociation, with no mention whatsoever of increased levels (i.e., final signals). There remains the labeling limit of, at most, one complementary reporter probe per binding site on the target molecule. Additionally, these investigators do not disclose any nucleic acid precipitation agents which possess capabilities such as inactivating nucleases, allowing proteases to function effectively, or strengthening binding, all which are further aspects to be provided by the reagents of the present invention.

Numerous modifications have been made to the original sandwich hybridization format, including replacing the filter with other solid supports (Rashtchian, A., Eldredge, J., Ottaviani, M., Abbott, M., Mock, G., Lovern, D., Klinger, J. and Parsons, G. (1987) Clinical Chemistry 33, 1526–1530) Langdale, J. A. and Malcolm, A. D. B. (1985) Gene 36, 210–220) and the use of affinity methods to improve the speed of the capture process (Rashtchian et al. (1987); Langdale and Malcolm (1985); Langer, P. R., Waldrop, A. A. and Ward, D. C. (1981) Proc. Natl. Acad. Sci. USA 78, 6633–6637; Manning, J., Pellegrini, M. and Davidson, N. (1977) Biochemistry 16, 1364–1370; Delius, H., van Heerikhuzen, H., Clarke, J. and Koller, B. (1985) Nucl. Acids Res. 13, 5457–5469; Dale, R. M. K. and Ward, D. C. (1975) Biochemistry 14, 2458–2469; Banfalvi, G., Bhattacharya, S. and Sarkar, N. (1985) Anal. Biochem. 146, 64–70; Arsenyan, S. G., Avdonia, T. A., Laving, A. Saarma, M. and Kisselev, L. L. (1980) Gene 11, 97–108). These formats all employ a single capture step. Insufficient specificity and sensitivity, however, remain problems for the clinical application of these techniques.

Another yet further aspect of the present invention is to provide assays employing new reagents which provide the necessary specificity and sensitivity for the clinical application of hybridization assays.

Another problem with the general application of conventional hybridization techniques results from the fact that different target nucleic acid sequences (and the corresponding complementary probes) vary considerably in (G+C) content. Consequently, since the hybrid melting temperature and the optimal hybridization temperature in commonly used assay reagents vary as a function of the (G+C) content, they will be different for target:probe combinations of different composition (assuming the sequence lengths are the same). This means that the optimal assay temperature in the standard assay reagents may be different for each assay. This is highly undesirable since it makes it very difficult to standardize the assay format to allow for the testing of many samples for different organisms in a common instrument at a single temperature. Although probe length can be varied somewhat to correct for differences in melting temperatures (among probes with widely differing (G+C) content), inclusivity and exclusivity requirements set practical limits on this approach.

It is another aspect of the present invention to provide regents and methods which employ a general assay protocol, e.g. temperature, for a wide range of tests which is unavailable with hybridization media in common use.

Melchior and von Hippel (Proc. Natl. Acad. Sci. USA, 70 (1973), 298–302) have observed that in solutions containing tetraalkylammonium cations the A:T base-pair is strengthened relative to the G:C basepair. Hamaguchi and Geiduschek (Jour. Amer. Chem. Soc. 84 (1962), 1329–1338) have reported that chaotropic anions denature nucleic acids and disrupt the A:T base pair more strongly than the G:C base-pair. These references, however, fail to disclose how the results may be utilized to provide reagents meeting the various aspects of the present invention and in particular fail to teach whether achieving GC/AT equivalence is desirable and if so, how it is to be achieved.

It is yet another aspect to overcome the limit of one reporter probe binding to each target site inherent in all heretofore available hybridization procedures.

It is still another aspect of the present invention to dramatically increase the level of signals that one can obtain in traditional hybridization assays.

All documents cited herein are fully incorporated herein by reference.

SUMMARY

In accordance with the various principles and aspects of the present invention there are provided herein novel organic salts and combination-salts, having unique and useful properties related to the hybridization and detection of nucleic acids. Listed below are the most useful properties of the preferred hybridization reagents of the present invention. Preferred embodiments are those reagents which possess the first listed property (1), and additionally at least two (2) of the remaining eight (8) properties.

Each preferred reagent possesses the following property: 1) use of the reagents of the instant invention in hybridization assays results in signals of significantly greater magnitude than those obtained in common reference reagents (SSC, SET, phosphate buffer or GuSCN). This observed phenomenon is referred to as hyperhybridization or superstoichiometric labeling, reflecting the fact that more than one reporter molecule is bound per available binding site on the target molecule. We have surprisingly discovered not only that the preferred reagents result in observance of this phenomenon but also that the source of the elevated signals is something other than, or in addition to, simple hybridization. Accordingly, hyperhybridization should be understood simply as a reference to very high signals obtained in the hybridization assay of the instant invention, and not as a statement that classical hybridization is the source of the strong signals.

Additionally, each preferred reagent of the instant invention possesses at least two (2) of the following properties:

1) It minimizes the background noise which can result from either non-specific hybridization (of non-complementary or partially complementary nucleic acids) or non-specific binding (for example, by electrostatic forces) of labeled reporter probe to solid supports.

Alternatively stated, the Signal-to-Noise (S/N) ratio obtained in the reagent is at least 25% greater than that obtained in a common reference reagent, such as GuSCN.

2) It inactivates nucleases. Specifically, after a 15-minute incubation at 37° C. with up to 12.5 ug/ml RNase A in the reagent, at least 50% of a population of target rRNA molecules remain intact, i.e., not cleaved by the RNase. This is especially useful in an assay involving nucleic acids, since nucleases could destroy targets and/or probes. The integrity of the nucleic acids is typically measured by their capturability.

3) It allows proteases to function effectively. This may be conveniently measured by either of two assays. (1) Indirectly: in the assay described in the immediately preceding paragraph, the addition of Proteinase K to a final concentration of 2.5 mg/ml results in there being at least 50% more intact rRNA than without the protease addition. (2) Directly: in the reagent, after the addition of Proteinase K to a final concentration of 2.5 mg/ml and a 10-minute incubation at 37° C., at least 50% of 5 mg/ml BSA is solubilized. Protease activity is advantageous because it potentially removes nuclease activity, helps disrupt target cells to expose target molecules, and/or aids in the deproteinization of nucleic acids, which can in turn increase hybridization signals and lower background.

4) It accelerates the speed of hybridization reactions by at least ~50% relative to commonly used reference reagents (e.g. GuSCN).

5) It increases bond strengths of A:T base-pairs relative to G:C base-pairs such that the bond strengths of the two types of pairs are approximately equivalent. This is ideally quantified by measuring the width of a nucleic acid melting curve, or by determining the melting temperatures of hybrids of different GC-content. Significant GC/AT equivalence is indicated, using probes approximately 35 nucleotides in length, by a standard melting curve width of 5° C. or less, or by a difference of less than 10° C. between the dissociation temperatures of probes with 37%-GC and 66%-GC. If exact equivalence obtains, then it follows that all probes of a given length will have approximately the same melting temperature ($T_d$) in the reagent. A primary advantage of this is that hybridization conditions for a broad range of assays, employing probes of widely different GC contents, can be standardized (for example, in an automated format) because, for probes of a given length:

a) All hybridizations proceed at essentially the same rate at a given temperature below $T_d$;

b) All hybridizations proceed to essentially the same extent during a fixed interval of time; and c) All hybridizations are essentially equally stringent.

It will be understood that there may be modest differences in the rate, extent and stringency of hybridization as a function of the exact nucleotide sequence of each hybrid due to differences in more complex interactions such as base stacking, interactions between chemically modified bases, etc.

6) It facilitates capture on solid supports, such as magnetic beads, advantageous for reversible target capture:

a) by promoting or accelerating the capture of poly-dA-tailed oligonucleotides on magnetic beads coated with oligo-dT. This is advantageous in the most preferred hybridization assay in which the solid support is oligo-dT-coated magnetic beads and in which poly-dA-tailed oligonucleotides, complementary to the desired target, serve as a bridge between the target and the solid support. This system is described in greater detail in European Patent Application No. 87309308.2; and b) by preventing the aggregation of magnetic beads in various matrices.

7) It lyses cells to expose target nucleic acids.

8) It deproteinizes nucleic acids to make them accessible for efficient hybridization. This helps to control non-specific backgrounds, since we have discovered protein-nucleic acid complexes are implicated in non-specific binding.

The novel organic salts of the present invention possess the first, and some or all of the rest of the above properties and preferably comprise at least two ions: a tetraalkylammonium (TAA) cation and a chaotropic anion.

The anions employed in the preferred reagents of the first invention ideally are those which denature nucleic acids (i.e., which are chaotropic) and include for example: Trichloroacetate (TCA), Thiocyanate (SCN), Trifluoroacetate (TFA), Perchlorate (PCA), and Iodide I.

The cations employed in the preferred reagents of the present invention ideally are those which strengthen A:T base pairs, such as the tetramethylammonium (TMA) or tetraethylammonium (TEA) ions.

Preferred embodiments of the present invention comprise TMA.TCA, TMA.TFA, TMA.SCN:TMA.TFA (a 1:1 mixture, abbreviated "$T^3$") and the most preferred embodiment, Guanidinium SCN (GuSCN):TMA.TFA (a 'family' of mixtures comprising these two salts in various relative concentration ratios, abbreviated "$GT^3$").

$GT^3$ is most preferred because it advantageously comprises the following characteristics:

1) it promotes superstoichiometric labeling;

2) it effects approximate GC/AT equivalence (Evaluations of GC/AT equivalence are based on two different types of information: (a) the sharpness of a melting curve(s) (the sharper the curve, the greater the degree of equivalence) and (b) the closeness of melting temperatures (Td's) of hybrids of different GC content (the closer the Td's, the greater the degree of equivalence));

3) it inactivates nuclease (RNase A);

4) it minimizes background/specificity problems;

5) it fosters efficient target capture on magnetic beads;

6) it accelerates hybridization relative to conventional reagents;

7) it is stable at room temperature and 37° C. for at least six months; and 8) with respect to its ability to lyse cells, the most preferred assay method comprises first lysing the target cells in 5M GuSCN, part of the $GT^3$ composition which is then advantageously completed by adding an equal volume of 4M TMA.TFA in which hybridization ideally takes place. Since GuSCN is an efficient lysis agent and $GT^3$ is a superior hybridization agent, such a protocol results in efficient lysis followed by superior hybridization.

Other preferred embodiments possess certain of the aforementioned desirable capabilities and accordingly each has clear utility in and of itself. (For example, a reagent that denatures nucleic acids but not proteins is ideally used in enzymatic amplification reactions.) In approximate order of decreasing preference they are: $T^3$, TMA.SCN, TMA.TFA, and TMA.TCA, all of which are still superior to standard hybridization solutions (SET, SCC, Phosphate or GuSCN) which have been used as reference. For example, GuSCN does not effect superstoichiometric labeling, does not accelerate hybridization to nearly the same extent, does not bring about GC/AT equivalence, and is not as suitable as a medium for bead capture since it requires greater dilution and causes some aggregation; SSC, SET, and Phosphate do not bring about superstoichiometric labeling, do not inactivate nuclease, do little to accelerate hybridization, do not equalize GC/AT base pairs, cause bead clumping, do not lyse cells and only moderately deproteinize nucleic acids.

A most preferred detection method suitable for use on an automated system comprises:

a) combining the sample to be analyzed with an entity which disrupts molecular structure, mixing thoroughly, and incubating at an appropriate temperature for an appropriate length of time, thereby exposing a target nucleic acid;

b) adding a specific capture probe, mixing thoroughly, and incubating at a temperature and length of time to permit hybridization of said probe to the target nucleic acid;

c) adding a solid support, mixing thoroughly, and incubating at an appropriate temperature for an appropriate length of time, so as to capture the hybrids on said solid support;

d) physically separating any uncaptured materials from the solid support;

e) adding a wash buffer, mixing thoroughly, and physically separating any unbound materials from the solid support; and repeating this step as often as desired;

f) adding to the solid support having attached targets a release buffer, mixing thoroughly, and incubating at an appropriate temperature for an appropriate length of time so as to cause said targets to be released from said solid support;

g) removing from the solid support the solution which contains the released targets and transferring said solution to a separate vessel;

h) adding a labeled (reporter) probe, mixing thoroughly, and incubating at an appropriate temperature for an appropriate length of time whereby hybridization of the reporter probe to the target can occur;

i) adding an entity which will effect superstoichiometric labeling, mixing thoroughly, and incubating at an appropriate temperature for an appropriate length of time;

j) adding a solid support, mixing thoroughly, and incubating at an appropriate temperature for an appropriate length of time, so as to capture the hybrids on said solid support;

k) physically separating any uncaptured materials from the solid support;

l) adding a wash buffer, mixing thoroughly, and physically separating any unbound materials from the solid support; and repeating this step as often as desired;

m) adding to the solid support with attached targets a release buffer, mixing thoroughly, and incubating at an appropriate temperature for an appropriate length of time, so as to cause said targets to be released from said solid support;

n) removing from the solid support the solution which contains the released targets, and transferring said solution to a separate vessel;

o) carrying out one or more additional capture/release cycle(s) (steps h through l) to reduce background (noise) levels;

p) optionally, dissolving the precipitates (which contain the targets and probes) and rendering the labeled probes monodisperse so that they are all accessible for detection;

q) adding appropriate chemical and/or biological reagents, simultaneously or sequentially, mixing thoroughly, and incubating at an appropriate temperature(s) for an appropriate length(s) of time so as to detect the superstoichiometrically labeled targets.

It will be recognized by those skilled in the art that various steps of the preceding procedure may be conveniently combined.

Further understanding may be had concerning the various properties of the preferred embodiments of the present invention by reference to the detailed Description.

| GLOSSARY | |
|---|---|
| Glossary of Abbreviations, Terms, and Probe Sequences Used: | |
| EDTA | — Ethylenediaminetetraacetic acid |
| Gu | — Guanidinium |
| GuSCN or GT | — Guanidinium thiocyanate |
| TCA | — Trichloroacetate |
| TEA | — Tetraethylammonium |
| TFA | — Trifluoroacetate |
| TMA | — Tetramethylammonium |
| TMA.TCA | — Tetramethyammonium:Trichloroacetate (this reagent can comprise any of a variety of concentrations of these ions; when not otherwise noted, the two ions are present in equimolar amounts at approximately 3M; ordinarily buffered with phosphate and borate, and/or EDTA) |
| TMA.TFA | — Tetramethyammonium:Trifluoroacetate (this reagent can comprise any of a variety of concentrations of these ions; when not otherwise noted, the two ions are present in equimolar amounts at approximately 4M; ordinarily buffered with phosphate, borate and EDTA) |
| TMA.SCN | — Tetramethyammonium:Thiocyanate (this reagent can comprise any of a variety of concentration of these ions; when not otherwise noted, the two ions are present in equimolar amounts at approximately 3M ordinarily buffered with phosphate, borate and EDTA) |
| $T^3$ | — TMA.TFA:TMA.SCN (a family of reagents comprising solutions of various concentrations of these two compounds; when not otherwise noted, a 1:1 mixture of TMA.TFA and TMA.SCN resulting in final concentrations of approximately 2M TMA.TFA and 1.5M TMA.SCN) |
| $GT^3$ | — GT:TMA.TFA (a family of reagents comprising solutions of various concentrations of these two compounds; when not otherwise noted, a 1:1 mixture of 5M GT and 4M TMA.TFA resulting |

GLOSSARY
Glossary of Abbreviations, Terms, and Probe Sequences Used:

| | |
|---|---|
| | in final concentrations of approximately 2.5M GT and 2M TMA.TFA) |
| GT³* | — GT:TMA.TFA (a member of the GT³ family of reagents; unless otherwise noted, a 2:3 mixture of GT and TMA.TFA resulting in final concentrations of approximately 2M GT and 2.4M TMA.TFA) |
| GT⁵ | — GT:TMA.TFA:TMA.SCN (a member of the GT³ family of reagents; unless otherwise noted, a 1:1:1 mixture of the three substituent reagents resulting in final concentrations of approximately 1.7M Gu, 3.7M SCN, 3.3M TMA and 1.3M TFA) |
| $T_d$ | — Dissociation (melting) temperature. |
| $\Delta T_{3/4-1/4}$ | — Melting curve width |
| RTC | — Reversible Target Capture |
| Hybridization | — The highly specific association of two mutually complementary single-stranded nucleic acid molecules. |
| Dissociation temperature | (used interchangeably with melting temperature) — The temperature at which 50% of the nucleic acid hybrids initially present in a population are dissociated. |
| Melting curve width | — By convention, the difference between the temperature at which 75% of a population of pre-formed, meltable hybrids remain associated and that at which 25% are still associated. |
| Chaotrope | — Large anions which, at high concentrations, or in some cases at low pH, disrupt the water lattice and thereby the structure of nucleic acids (lowering their dissociation temperature) and/or proteins (lowering their transition temperature). |
| Capture probe | — A nucleic acid molecule comprising two moieties: one part which can hybridize to a target molecule, and an attached part which can bind to a solid support. (In the preferred assay of the present invention the latter part is a poly-dA 'tail' which can bind reversibly to oligo-dT-coated magnetic particles.) |
| Reporter probe | — A nucleic acid molecule 'labeled' with a detectable entity (e.g. fluorophere, radioactive isotope or an antigen to which an enzyme-antibody conjugate can bind) which can hybridize to a target molecule. |
| Riboprobe | — A single-stranded RNA molecule typically made by in vitro transcription (such as by using SP6 or T7 RNA Polymerase) of a portion of a vector containing the appropriate DNA segment. The preferred riboprobes used herein are exactly complementary to either the 3'- or 5'-half of E. coli 16S ribosomal RNA and are able to hybridize with all eubacterial rRNAs tested by virtue of several universally conserved sequences in the 16s rRNAs of eubacteria, (the prefix in the designation of the Riboprobe indicates the portion of the rRNA to which it is complementary), and are labeled with 32P, biotin or fluorescein. |
| BioRiboprobe | — A Riboprobe containing biotinylated nucleotides. |
| FluoroRiboprobe | — A Riboprobe containing fluorosceinated nucleotides. |
| Reversible Target Capture | — A process in which target nucleic acids are purified by sequential cycles of capture on and release from various solid supports as disclosed in detail in European Patent Application No. 37309308.2. |
| Hyperhybridization | — The phenomenon of a hybridization assay giving rise to signals of greater magnitude than usually observed in a reference reagent such as GuSCN or 6x SET |
| Superstoichiometric labeling | — A more precise and accurate term to describe "hyperhybridization," reflecting the fact that the 'hyper-signals' are due to a type of binding other than true hybridization (probably co-precipitation) and that more than one labeled probe is bound per accessible target site. |

| Probe | Target | Sequence (5' → 3') |
|---|---|---|
| R444 | E. coli | AAT GAG CAA AGG TAT TAA CTT TAC TCC CTT CCT CCC C |
| 666 | List. | TGT CCC CGA AGG GAA AGC TCT GTC TCC AGA GTG GTC AAA GAT AT |
| 676 | Salmon. | TCA ATT GCT GCG GTT ATT AAC CAC AAC ACC TTC CT |
| 730 | E. coli | TAA CGT CAA TGA GCA AAG GTA TTA ACT TTA CTC CC |
| 732 | Campy. | TCC AAC TGT TGT CCT CTT GTG TAG GGC AGA TTA AC |

-continued

| Probe | Target | Sequence (5' → 3') |
|---|---|---|
| 733 | Campy. | TGT GTT AAG CAG GAG TAT AGA GTA TTA GCA GTC GT |
| 787 | E. coli | TCA ATG AGC AAA GGT ATT AAC TTT ACT CCC TTC CT |
| 853 | E. coli | ACG GTC CAG ACT CCT ACG GGA GGC AGC AGT GGG GA |
| 854 | E. coli | TCC CCA CTG CTG CCT CCC GTA GGA GTC TGG ACC GTA TAT |
| 855 | E. coli | GGG AGT AAA GTT AAT ACC TTT GCT CAT TGA CGT TA |
| 1009 | Campy. | C*AT TCA CCG TAG CAT GGC TGA TCT ACG ATT ACT C*T |
| 1010 | Campy. | C*CC GAA CTG GGA CAT ATT TTA TAG ATT TGC TCC C*T |

C* indicates a modified Cytidine residue

BRIEF DESCRIPTION OF THE DRAWINGS

Further understanding of the various aspects and principles of the present invention may be had by reference to the drawings wherein.

I. GuSCN:TMA.TFA("$GT^3$")

Figure 1:
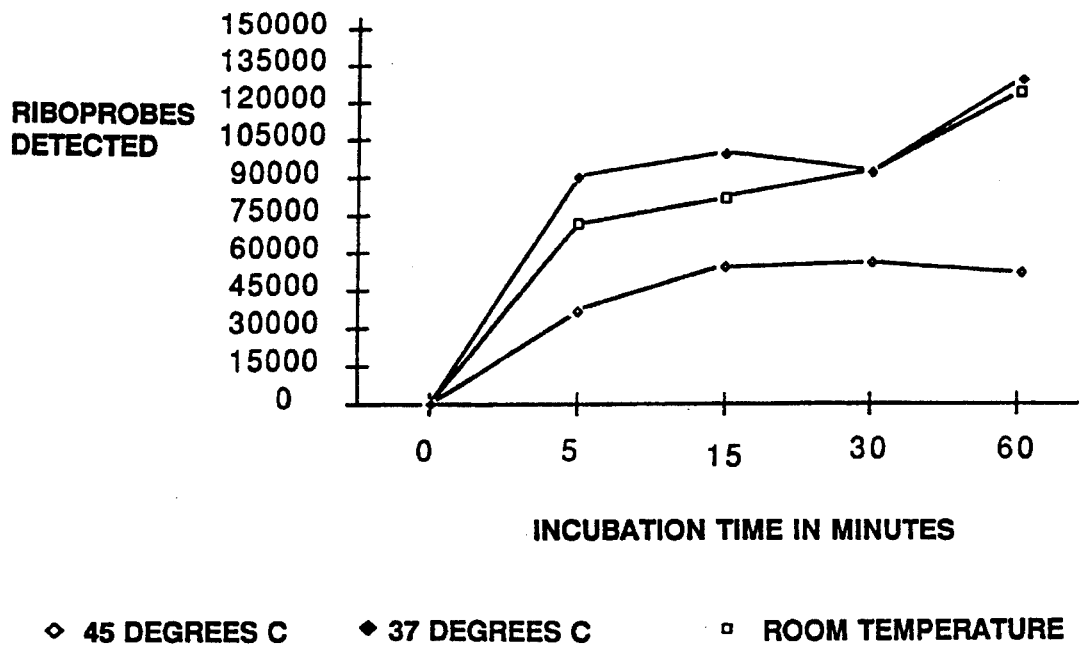
FIG. 1 shows hybridization in $GT^3$ as a function of temperature.

A reagent containing equal parts of 5M GuSCN and 4M TMA.TFA (hereinafter abbreviated as "$GT^3$") is the most preferred reagent embodiment of the present invention. It provides excellent RNase-control characteristics and support of efficient and specific hybridization including "super-stoichiometric labeling": the binding of more than one detectable molecule of probe to each target site on each target molecule. Indeed, the experiments described below demonstrate that $GT^3$ meets all of the objectives in terms of desired properties previously listed.

This reagent advantageously utilizes in synergy the properties of its individual components: GuSCN, known to have desirable RNase-inhibiting properties; and TMA.TFA, which was found to possess the ability to accelerate and enhance hybridization (section 5). It was surprisingly found that $GT^3$ possesses all the properties of its individual components, contrary for example to the less preferred TMA.TFA.

A. General Methods

In the various experiments described herein, the following general protocols were followed. Variations from these procedures are described in those experiments where they occur.

DNA:RNA Hybridization

1) The following were combined: reagent, Dextran Sulfate (to a final concentration of 10%), rRNA target (cell extracts at a defined concentration) and reporter probe ($^{32}$P-labeled 3'-Riboprobe). The mixture was incubated to bind the reporter probes to the target rRNA.

2) The capture probe (dA-tailed oligomer) (see European Appliction No. 87309308.2) was added and the mixture was incubated at the desired temperature.

3) Aliquots were removed at defined times and added to oligo-dT-coated 1μ magnetic beads obtained from Advanced Magnetics pre-warmed to 37° C. if their volume was equal to or greater than that of the hybridization mixture. A small volume (e.g. equal to or slightly less than the volume of the sample aliquot) of concentrated beads was used for capture in TMA salts, while a large volume (e.g. twice that of the aliquot) of more dilute beads was used for capture in GuSCN. The resulting mixture was incubated for three minutes to capture the hybrids on the beads.

4) The beads were separated magnetically using a magnetic separator such as is commercially available from Corning or that described in copending U.S. Ser. No. 121, 191 and the supernatant removed. The beads were washed twice with wash buffer between 0.5M or 2M GuSCN. The beads were resuspended in wash buffer and the amount of radioactivity bound to the beads was determined by a scintillation counter.

5) Using the specific activity [cpm/fmole] of the Riboprobe, the number of Riboprobes captured was calculated. Then, knowing the number of cells in the sample, the number of riboprobes captured per cell was calculated. (Prior to use in these experiments, the concentration (cells/ml) of each freshly grown cell preparation was determined by serial dilution, growth on solid media and colony counting. Solutions of cells were then combined with GuSCN (to a final 2.5M) and stored at −20° C. until needed for experiments.)

At the outset of this work, it was assumed that one Riboprobe was bound to each molecule of 16S rRNA, implying a 1:1 Riboprobe:ribosome ratio. However, in a variety of experiments abnormally high numbers of riboprobes per cell were seen (e.g., significantly greater than the accepted norm of 10,000–20,000 ribosomes/cell in Salmonella). As will be discussed below, this was discovered to be due to the fact more than one Riboprobe was bound to each molecule of 16S rRNA. To reflect this discovery, "Riboprobes captured/bound per cell" are reported herein rather than "Ribosomes bound per cell."

Melting and Elution Studies

1) Reagent for the present invention (herefter "reagent") Dextran Sulfate (to a final concentration of 10% by weight), nucleic acid target (rRNA from cell extracts at a defined concentration, or an artificial target comprising a $^{32}$P-labeled oligomer), and if the target was rRNA, a $^{32}$P-labeled 3'-Riboprobe, and a capture probe (dA-tailed oligomer) were combined, and the mixture incubated for at least an hour at 37° C. to allow hybridization to occur.

2) The mixture was diluted 1:10 with the reagent (without Dextran Sulfate), and held at the hybridization temperature for the remainder of the experiment.

3) Approximately 0.20 ml Aliquots were removed from the mixture and incubated at various elevated temperatures, e.g. 40° C. to 95° C., for six (6) minutes.

4) To each heated aliquot, immediately after the six-minute incubation, and periodically to aliquots taken from the constant-temperature mixture (No. 2 above) 10 μl magnetic beads were added at a concentration of about 100 O.D. 550/ml. The mixtures were incubated at the designated temperatures, and the beads were separated, washed and counted as above (#3 & #4). The constant temperature-mixture measurements served as a baseline to make sure that the level of hybridization was not changing with time. At each elevated temperature, the amount of hybridized target nucleic acid, relative to the constant-temperature reference, was determined.

5) For elution experiments, a 200 μl aliquot was taken from the constant-temperature mixture, 10 μl of beads were added and incubated, the beads were separated magnetically, and the supernatant was removed. An equal volume of 2.5M GuSCN was added to the beads and the mixture was incubated at 37° C. for 5 min. The beads were separated magnetically and the supernatant was removed. The beads were resuspended in wash buffer, the beads and the supernatant were counted in a scintillation counter, and the percent elution was calculated.

B. Bead Capture

Experiments to be described below demonstrated that when hybridization was carried out in TMA.TFA, capture by oligo-dT-coated magnetic beads was possible without any dilution of the reagent: i.e., simply by adding a small volume of concentrated beads (much smaller than the volume of the hybridization mixture) and incubating. This was a very advantageous property of the reagent, and an unexpected improvement over GuSCN which must be diluted three-fold for capture. To determine whether capture would take place in $GT^3$ without dilution, or how much dilution would be necessary, target and probes were hybridized to completion in $GT^3$, after which aliquots of the hybridization mixture were taken and combined with various volumes of oligo-dT-coated magnetic beads of various concentrations (such that the total amount of beads was the same in each case). After three minute incubations at 37° C., the beads were washed twice and counted.

Table 1 presents the averaged results from three separate experiments, listing the amount of hybrids captured with various volumes of beads, relative to the amount captured with two volumes of beads ("one volume" means a volume equal to the volume of the hybridization mixture aliquot); numbers in parentheses are standard errors of the data.

TABLE 1

| Bead capture in $GT^3$ | |
| --- | --- |
| Bead volume | Relative amount of complex captured |
| 2x | [100%] |
| 1x | 93% (+/−8%) |
| 0.5x | 55% (+/−15%) |
| 0.25x | 59% (+/−16%) |

These results show that with this reagent one need add only one volume of beads to one volume of hybridization mixture (i.e., dilute the reagent by ½) in order to capture complexes efficiently.

C. Proteinase K Activity

Proteinase K (PK) is moderately active in, while ribonuclease is significantly inhibited by, GuSCN. Prior to empirical determination, it could not be predicted whether addition of the GuSCN to TMA.TFA would produce a reagent with the capability of controlling nucleases. The extent of Proteinase K activity in $GT^3$ was assayed by determining its ability to digest (solubilize) $^{14}$C-labeled bovine serum albumin (BSA).

The results of our experiments are presented in Table 2 below. These experiments were done twice, and the percentages below are the averages of the two experiments; the numbers in parentheses are the experimental variations.

TABLE 2

| Proteinase K activity in various reagents | |
| --- | --- |
| Reagent | % BSA solubilized |
| GuSCN | 41% (+/−10%) |
| $GT^3$ | 92% (+/−1%) |

The results indicate a high level of PK activity observed with $GT^3$. In another experiment it was observed that approximately 40% of the initial Proteinase K activity remained after incubation of the enzyme in $GT^3$ at 37° C. for two hours. This contrasts favorably with a similar incubation in GuSCN, after which only 10% of the initial activity remained. This demonstrates a clear and unpredictable advantage of $GT^3$ over GuSCN, since whenever lengthy digestions are required for efficient cell lysis and deproteinization, the reagent in which Proteinase K is more stable will be more advantageous.

Subsequent experiments showed that Proteinase K is similarly active in a related reagent, $GT^5$, a 1:1:1 mixture of 5M GuSCN, 4M TMA.TFA and 6M TMA.SCN. It has also been observed that the level of Proteinase K activity gradually decays upon incubation at 37° C. in this reagent, with a half-life of approximately 2 hours. Again, this is a significant advantage over GuSCN, in which the half-life is less than an hour.

D. Ribonuclease Activity

Though the ability of a hybridization medium to support protease activity is desirable, an equally (or more) important property is the capability of inhibiting nucleases, especially ribonucleases. In this section experimental evidence is presented indicating that $GT^3$ and $GT^5$ both inhibit the activity of a typical ribonuclease, RNase A. In the first experiment reported in this section, in addition to assaying nuclease activity in $GT^3$ and in $GT^5$, a full set of control reactions was performed in GuSCN (an established inhibitor) and phosphate buffer (in which the enzyme is known to be active). The experimental protocol was a follows:

1) A target complex was prepared by hybridizing target rRNA (from Salmonella extracts), capture probe (dA-676), and $^{32}$P-labeled 3'-Riboprobe (as earlier described).

2) The target complex was diluted into each of the above four test reagents.

3) RNase A solutions of various concentrations (0–250 μg/ml in 0.15H phosphate buffer pH7) were prepared. Into tubes of the diluted target complex was added RNase A, to one of the final concentrations noted in Table 3 below. The control comprised only phosphate buffer diluent. The mixtures were incubated at 37° C. for 15 minutes. Proteinase K was added to a final concentration of 1.25 mg/ml to stop the nuclease activity.

4) Tailed probes and hybridized complexes were captured on magnetic beads (as previously described), which were washed and counted. The level of RNase inhibition was calculated as follows.

$$\% \text{ RNase inhibition} = 100 \times \frac{(\text{cpm captured } (+R\text{Nase})}{(\text{cpm captured } (-R\text{Nase})}$$

Table 3 presents the data from this experiment,

TABLE 3

| [RNase A] | RNase A inhibition in various reagents % RNase inhibition | | | |
|---|---|---|---|---|
| ug/ml | Phosphate | GuSCN | $GT^3$ | $GT^5$ |
| 0.00 | 100% | 100% | 100% | 100% |
| 0.13 | 0.84% | 100% | 100% | 100% |
| 1.25 | 0.05% | 100% | 100% | 100% |
| 4.17 | 0.52% | 100% | 100% | 100% |
| 12.50 | 0.06% | 100% | 100% | 93% |

These data demonstrate that $GT^3$ exhibits potent inhibition of RNase A. Additionally, this experiment demonstrates that $GT^5$ also possesses nearly the same RNase inhibitory capabilities. The data also show that there is considerable flexibility in adjusting the relative concentrations of various components of the reagent(s) in order to retain the desired nuclease control.

E. Hybridization in $GT^3$

Since there was no certainty that hybridization would take place efficiently in $GT^3$, experiments were undertaken to so determine.

1) Hybridization temperature optimization

In this section, data are reported from experiments to determine which of three potential reaction temperatures (room (22°–24° C.), 37° C. and 45° C.) best promoted hybridization. In these experiments, the target was rRNA from Salmonella extracts at $9 \times 10^6$ cells/ml, the reporter probe was a $^{32}$P-labeled 3'-Riboprobe at 1 ug/ml, and the capture probe was dA-tailed oligo 676 (see U.S. Ser. No. 127,484 for further details) at 0.5 ug/ml. Target and riboprobe were incubated at 37° C. for 4 hours to prehybridize them, after which various aliquots of the mixture were either kept at the same temperature or re-equilibrated at one of the other temperatures. Capture probe was then added to each, timed incubation was begun and aliquots were removed after 5, 15, 30 and 60 minutes. The removed aliquots were added to an equal volume of magnetic beads (pre-warmed to 37=C), mixed and incubated at 37° C. for three minutes to capture the hybridized complexes. The beads were then washed twice and counted. From the number of cpm captured, the specific activity of the riboprobe and the cell concentration, the number of riboprobes captured per cell was calculated for each time/temperature point. Three controls were done at each temperature: omitting the capture probe, omitting target cells/rRNA and substituting heterologous cells (E. coli) for the true target. The results of these experiments are presented in FIG. 1.

From these plots, 37° C. appears to be the optimized hybridization temperature followed closely by room temperature. This is especially advantageous since 37° C. is optimal for an instrument-based assay. The data also show that temperature between room temperature and 37° C. may be alternately preferred. This embodiment therefore provides considerable flexible in designing and performing a hybridization assay.

Further, the numbers of labeled probes captured per cell (>100,000) in this experiment are exceptionally high. Apparently the reagent assists the capture of approximately 10 riboprobes per 16S rRNA molecule target in these cells.

2) Hybridization in $GT^3$ and other reagents

For these experiments, target rRNA (from various cell extracts) was incubated for three hours with 1 ug/ml $^{32}$P-labeled 3'-Riboprobe (selected in accordance with the target rRNA as set forth in the Glossary) in the reagent of interest with 10% (mass/volume) Dextran Sulfate at 37° C. The dA-tailed capture probe was then added to a final concentration of 0.25–0.50 ug/ml, and the mixture was incubated at 37° C. Finally, the hybridization complex was captured on magnetic beads (two volumes of beads per volume of hybridization mixture), washed, and the extent of hybridization determined by scintillation counting. For all experiments, three controls were done: (1) a reaction in which the target rRNA was omitted, (2) a reaction in which the capture probe was omitted, and (3) a reaction in which heterologous cells (cells other than those for which the capture probe was specific) were substituted for the experimental target cells. Various reagents were tested, as listed below.

The results from these experiments are presented in Table 4. The number of riboprobes bound per cell was calculated from the following known or determined quantities: cpm/fmole of riboprobe, cells per reaction, and cpm captured per reaction. For each control, the captured "noise" as a fraction of "signal" was calculated.

TABLE 4

| Hybridization in various reagents | | | |
|---|---|---|---|
| Target cells: | Salmonella $8.5 \times 10^6$/ml | Campylobacter $1 \times 10^7$/ml | E. coli $8 \times 10^6$/ml |
| Capture Probe: | dA-676 0.5 ug/ml | dA-732 0.5 ug/ml | R444 0.25 ug/ml |
| Control cells: | E. coli $8 \times 10^7$/ml | E. coli $8 \times 10^7$/ml | Salmonella $8.5 \times 10^6$/ml |
| Reagent | | | |
| 75% 5M GuSCN | Ribos./cell: 1,000 | 500 | 2,100 |
|  | N/S, no trg.: 56% | 54% | 6% |
|  | N/S, no prb.: 78% | 63% | 12% |
|  | N/S, het. cells: 83% | 62% | 8% |
| 75% 5M GuSCN 25% 4M TMA.TFA | Ribos./cell: 900 | | |
|  | N/S, no trg.: 33% | | |
|  | N/S, no prb.: 33% | | |
|  | N/S, het. cells: 56% | | |
| 50% 5M GuSCN 50% 4M TMA.TFA "GT³" | Ribos./cell: 220,000 | 90,000 | 130,000 |
|  | N/S, no trg.: 5% | 4% | 10% |
|  | N/S, no prb.: 0.2% | 0.1% | .5% |
|  | N/S, het. cells: 2% | 4% | 23% |
| 25% 5M GuSCN 75% 4M 4M TMA.TFA | Ribos./cell: 130,000 | | |
|  | N/S, no trg.: 79% | | |
|  | N/S, no prb.: 0.4% | | |
|  | N/S, het. cells: 6% | | |
| 4M TMA.TFA | Ribos./cell: 170,000 | | |
|  | N/S, no trg.: 79% | | |
|  | N/S, no prb.: 0.3% | | |
|  | N/S, het. cells: 4% | | |

5M GuSCN and 4M TMA.TFA were used as the stock solutions to prepare the reagents. The composition of each reagent shown in Table 4 is that before addition of the probe solution and the bacterial extract, which addition caused a 1.5-fold dilution of the reagent. In other experiments disclosed herein, the dilution fold was kept between 1.5 to 1.66. Also, the percentages refer to volumes of the stock solutions.

These results show that $GT^3$ is the most preferred hybridization reagent. Additional observations are:

a) Hybridization in $GT^3$ is significantly superior to that in GuSCN. The number of riboprobes captured per cell is exceptionally high.

b) The backgrounds are almost all very low in $GT^3$, demonstrating the specificity of the hybridization. The favorable background control is a feature that distinguishes the $GT^3$ (50:50 mixture) from reagent mixtures with a higher concentration of TMA.TFA.

The experiments just discussed indicated that as a hybridization reagent $GT^3$ was clearly superior to GuSCN. Those experiments were repeated for $T^3$ ($GT^3$ without GuSCN), $GT^5$ (a 1:1:1 mixture of 5M GuSCN, 4M TMA.TFA and 6M TMA.SCN). The experimental protocol was exactly as above except: the incubation with target and riboprobe only was done overnight rather than for four hours, and the-incubations were at 37° C. in $GT^3$ and $GT^5$ and at 45° C. in $T^3$. The results of these experiments shoved that the rate and the extent of hybridization were greater in $GT^3$ than in $T^3$ or $GT^5$.

3) Signal-to-noise (S/N) ratios

The following experiment demonstrates that not only does one obtain strong signals in $GT^3$, but also at an advantageous S/N ratio. The protocol was exactly as above (37° C. incubations, with a 3½-hour target+riboprobe pre-incubation). The results obtained are presented in FIG. 2. The controls were: capture probe omitted (+), target cells omitted (diamond), and heterologous (*E. coli*) rRNA substituted for the true target (Salmonella) rRNA (triangle). For reference, 300,000 cpm corresponds to approximately 172,000 riboprobes bound per cell.

Figure 2:
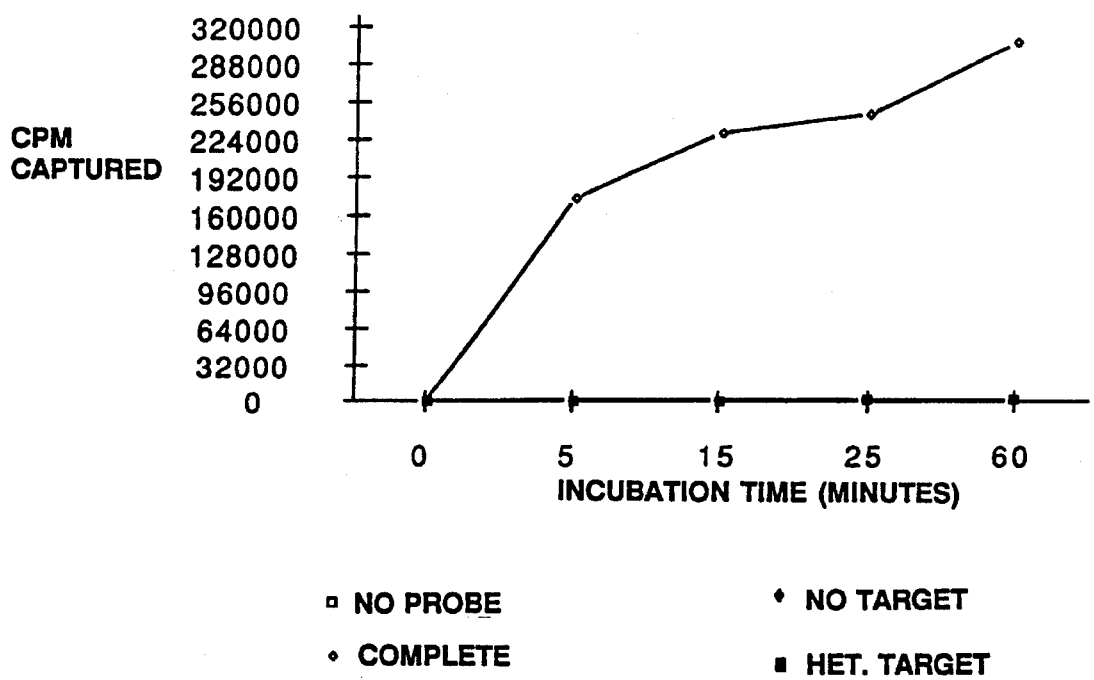
FIG. 2 graphically compares hybridization in $GT^3$ with a variety of controls.

As can be seen in FIG. 2, the controls were, as hoped for, quite low relative to the signal. In this experiment, the "no cell" and "heterologous cell" controls gave noise at 0.7–1.3% of the signal and the "no probe" control gave noise at 0.07–0.5% of the signal.

4) Reversible Target Capture and Signal-to-Noise Enhancement

The reduction of background levels is essential if one wishes to fully exploit the hyperhybridization potential of the new reagent(s). One way to reduce backgrounds is to take advantage of Reversible Target Capture (RTC): after the first capture, to elute (with 2.5M GuSCN, at 37° C.) and recapture (with two volumes of beads at 37° C.) the probe-target complexes, repeating this cycle as often as necessary to achieve the desired S/N ratio. The utility of this assay procedure was evaluated in the following experiment.

Protocol for Hybridization and Elution/Recapture

Hybridizations were performed using the generic eubacterial 5'-riboprobe, dA-tailed oligonucleotide #666 and either *E. coli* alone ($10^8$ cells/ml; control) or *E. coli* (E.C.) ($10^8$/ml) and *Listeria monocytogenes* (L.M.) ($3\times10^6$ cells/ml). Cell extracts had been prepared by lysis with lysozyme and mutanolysin, followed by Proteinase K. Hybridization was for 15 minutes at 37° C. Prewarmed magnetic beads (binding capacity: 1 ug/ml $dA_{12}$) were added (one volume for $GT^3$ captures and two volumes for GT captures) and capture was effected by incubation at 37° C. for 3 minutes. After magnetic separation, the beads were washed three times, and then the hybrids were eluted by adding one volume of 2.5M GuSCN and incubating for 1 minute at 37° C. For recapture, two volumes of beads were added and the mixture was incubated for 3 minutes at 37° C. The first and second sets of beads were scintillation-counted, as was the material which was eluted from the first set of beads but did not rebind to the second set. For each sample, the number of counts initially bound to the first set of beads was calculated by adding the final counts still bound to both sets of beads, and the counts eluted from the first set but not bound to the second. Similarly, the total counts eluted from the first set of beads were calculated by adding the un-re-bound elute counts and the counts on the second set of beads. The data from this experiment are presented in Table 5.

TABLE 5

| Hybridization and Elution/Recapture in GT and $GT^3$ | | | | |
|---|---|---|---|---|
| | GuSCN Signal (L.m. + E.c.) | GuSCN Noise (E.c.) | $GT^3$ Signal (L.m. + E.c.) | $GT^3$ Noise (E.c.) |
| Counts initially bound to first set of beads | 23,000 | 11,100 | 168,900 | 10,900 |
| Counts eluted from first set of beads | 15,600 | 510 | 105,800 | 700 |
| Counts bound to second set of beads | 4,500 | 30 | 87,200 | 45 |

These results clearly demonstrate the advantage gained with elution/recapture. In $GT^3$, for example, the Signal-to-Noise ratio increased from 15:1 after the first capture to almost 2000:1 after the second capture. This illustrates how assays in $GT^3$ can be modified to most fully capitalize on the hyperhybridization phenomenon. It is worth noting that the S/N ratios in $GT^3$ after one and after two rounds of capture are more than ten times better than with convention hybridization in GuSCN.

Without wishing to be bound thereby it is our hypothesis that the basis of $GT^3$ hyperhybridization is RNA precipitation. Assuming that this was the underlying mechanism, a further modification was made to the assay to circumvent non-specific precipitation of competitor molecules in biological samples. The following protocol reflects this modification.

Figure 4:
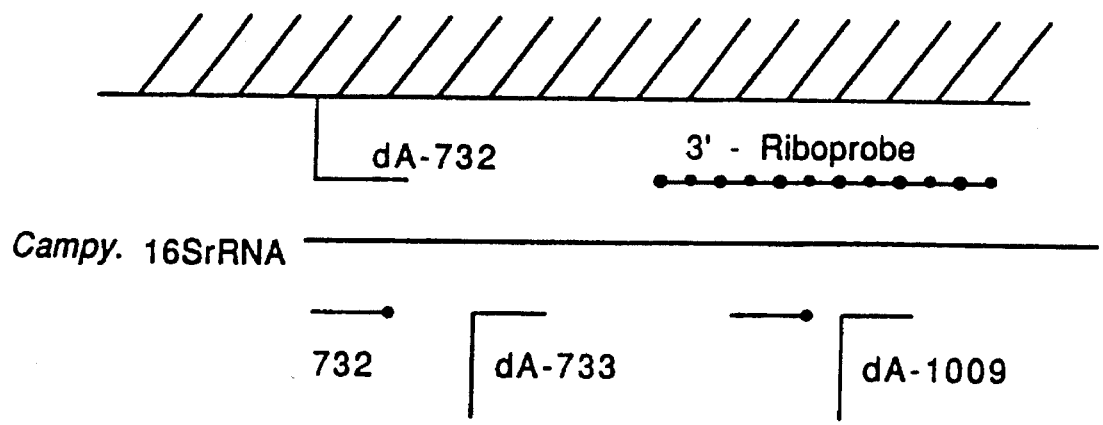
FIG. 4 graphically depicts the interplay of various probes in a preferred assay.
Figure 5:
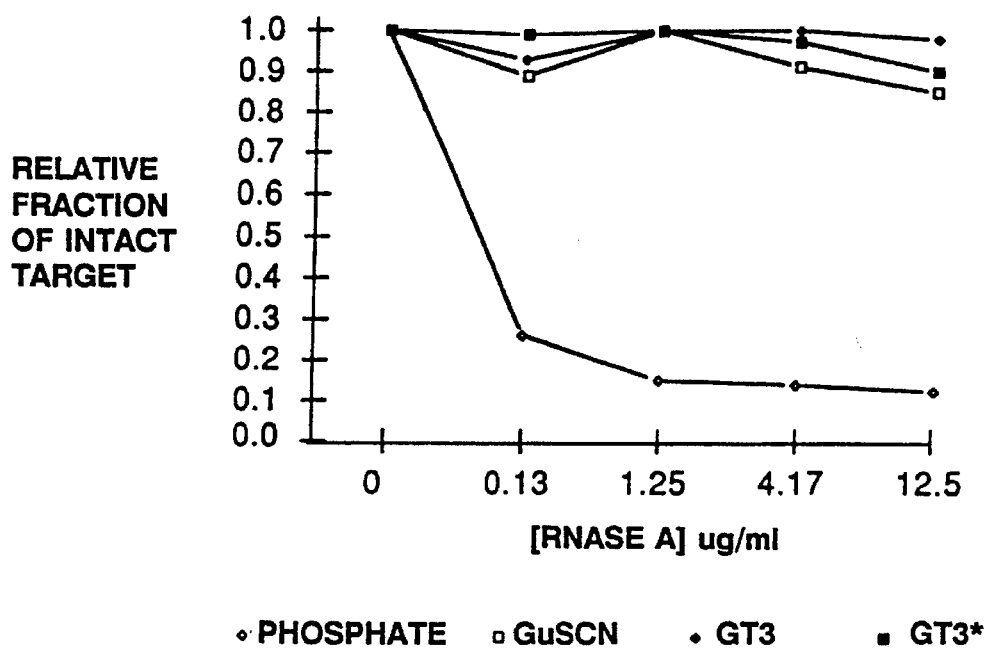
FIG. 5 graphically depicts RNase A activity of various reagent embodiments of the present invention.

Since large quantities of RNA may be present in biological specimens and since $GT^3$ can precipitate RNA, the targets and capture probes were first hybridized in GuSCN, and captured on the solid support. Then, the target-probe complex was washed and eluted (in 2.5M GuSCN) from the solid support, 4M TMA-TFA and riboprobe were added (the solution then approximated $GT^3$), and the mixture was incubated. The intent was to produce strong signals (due to hyperhybridization) and minimal backgrounds. Specific experimental details were as follows:

*Campylobacter jejuni* (final concentration: $10^7$ cells/ml) and *E. coli* (final concentration: $10^8$/ml) extracts were combined in either 2.5M GuSCN (GT) or $GT^3$. Control experiments contained no Campylobacter extracts. In the first round of hybridization and capture, two Campylobacter-specific oligonucleotide probes were used (see U.S. Ser. No. 216,679): $^{32}$-labeled oligonucleotide #732 and dA-tailed #733. (For an illustration of the probe reactivity scheme, see FIG. 4 and discussion pertaining thereto.) The probe-target complexes were eluted from the beads with 2.5M GuSCN. An aliquot of the eluate was scintillation-counted. Next, the eluted complexes were hybridized with $^{32}$P-labeled 3'-Riboprobe in either GT or $GT^3$. Finally, the hybrids were captured on a second set of beads, and the beads washed and counted. The number of probes captured per cell can be calculated from the cell concentration and the specific activity of the labeled probe. The results are presented in Table 6.

TABLE 6

Preliminary target: DNA-probe hybridization in GT or GT$^3$
followed by target: RNA-probe hybridization in GT or GT$^3$

| | First round: Reporter probe = oligonucleotide | | | | Second Round: Reporter probe = riboprobe | | | |
|---|---|---|---|---|---|---|---|---|
| Reag. | Sig. (cpm) | Noise (cpm) | Probes per cell | S/N | Reag. | Sig. (cpm) | Noise (cpm) | Probes per cell | S/N |
| GT | 11,600 | 5,600 | 4,600 | 2:1 | GT | 32,600 | 2,100 | 530 | 16:1 |
| | | | | | GT$^3$ | 1,200,000 | 10,300 | 19,500 | 120:1 |
| GT$^3$ | 16,400 | 2,200 | 6,500 | 7:1 | GT | 92,000 | 2,300 | 1,500 | 40:1 |
| | | | | | GT$^3$ | 2,130,000 | 37,900 | 34,700 | 56:1 |

These data support the following:

a) The first hybridization of an assay may be advantageously performed in GuSCN provided it is followed by a second in GT$^3$, with hyperhybridization taking place in the second step.

b) Hyperhybridization did indeed take place in a reagent formed by the addition of TMA.TFA to GuSCN after chemical elution in the latter. (This medium is similar in composition to 1:1GT$^3$ and belongs to the family of GT$^3$ reagents.)

c) The fact that hyperhybridization occurred after the probe-target complex was purified from cellular debris by a round of target capture indicates that it does not require high concentrations of cellular components such as proteins, etc.

d) Hyperhybridization took place in GT$^3$ when the labeled probe was an RNA molecule (riboprobe), but not when it was a short (DNA) oligonucleotide. (Compare Round 1 and Round 2 numbers.) Campylobacter cells were estimated to contain approximately 5,000 ribosomes each. The number of probes captured per cell in GT$^3$ in the first round (with a DNA labeled probe) was not very much greater than this or the same number in GT. The number of probes per cell in GT$^3$ in the second round (with an RNA labeled probe) was considerably greater than this, indicating hyperhybridization.

e) Not only were the signals stronger when hybridization took place in GT$^3$ with a labeled RNA probe (i.e. when there was hyperhybridization), but the S/N ratios were also greater. (Compare to the results presented in Table 5).

5) Capture probe concentration

Figure 3:
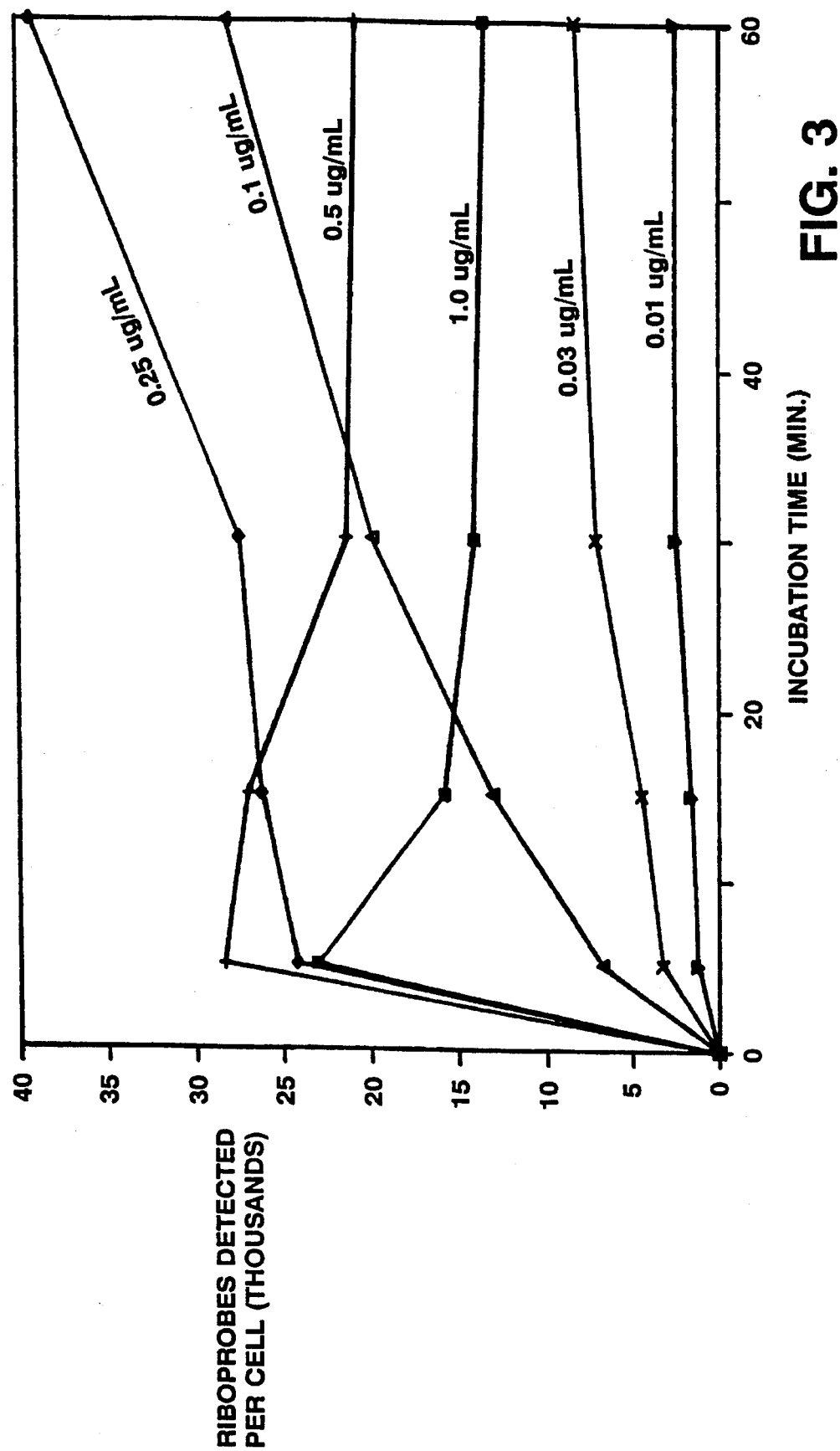
FIG. 3 graphically depicts hybridization in $GT^3$ as a function of capture probe concentration.

It is generally desirable to know how much capture probe is preferably used in order to capture the majority of available targets in a short period of time. If, as was found to be the case in other TMA reagents, acceptably efficient hybridization takes place at much lower probe concentrations than in GuSCN, there is the potential of significantly reducing the cost of the assay. To determine whether this was the case in GT$^3$, a series of hybridization assays were done following the protocol outlined in section 1.A. Salmonella extracts at 9×10$^6$ cells/ml, Riboprobe at 1 ug/ml, and dA-676 capture probe at various concentrations were used for the test. The only changes made were the following. The preliminary hybridization, involving only rRNA and riboprobe, was done overnight. Control target (E. coli rRNA) was present in all reaction mixtures, not just mixtures of "heterologous cells", in order to more closely approximate 'real world' conditions, eg conditions under which one is looking for a specific target in a sea of background. Finally, varying amounts of capture probe were added to the reaction mixtures, resulting in final concentrations of 0–1.0 ug/ml. The results are shown in FIG. 3. Probe concentrations in the legend are in ug/ml.

From this experiment, one can see that approximately 0.25 ug/ml is the optimal capture probe concentration. At lower concentrations, the hybridization rate and levels were not quite as advantageous. At higher concentrations, and after a short period of rapid hybridization, the amount of captured signal actually began to drop indicating the lowered desirability of such higher concentration of probe.

It may be noted that in the experiment presented in FIG. 3, the highest number of ribosomes (riboprobes) captured per cell was 35–40,000, somewhat lower than in other experiments done with this reagent. A subsequent experiment showed that the reason for this was the presence in the reaction mixtures of heterologous cells whose rRNA could hyper-hybridize to the riboprobes, thus removing from the mixtures a considerable fraction of the capturable signal. Without any heterologous cells present, the number of riboprobes captured per cell was greater than 100,000, as had been observed previously. This observation underscores the importance of the protocol wherein potentially competitor rRNA's are ideally removed prior to hyperhybridization (Table 6).

6) Dose-Response: *Campylobacter jejuni*

In order to demonstrate the clinical utility of this assay, a dose-response experiment was done. Various dilutions of *Campylobacter jejuni* extracts were probed for in a standard assay format, e.g. 10$^4$–10$^6$/ml. Each assay tube contained E. coli extracts at 1.6×10$^7$ cells/ml as competitors. Extracts and $^{32}$P-labeled 5'-Riboprobe were initially incubated at 37° C. for 30 minutes, after which dA-tailed capture probe #732 (Campylobacter-specific) was added and the mixture incubated for an additional 30 minutes. After this, the hybridized complexes were captured on magnetic beads. In one set of assays, at this point the amount of $^{32}$P bound to the beads was determined by scintillation counting (results below under "single capture"). In a parallel set of assays, the complexes were eluted from the beads with 2.5M GuSCN and recaptured on fresh beads, and the beads were counted (listed below under "second capture"). The data are presented in Table 7.

TABLE 7

Dose-Response with Campylobacter extracts

| Target Cells per sample | cpm captured | Signal to Noise | cpm captured | Signal to Noise |
|---|---|---|---|---|
| 1.09 × 10$^6$ | 696,000 | 93:1 | 304,000 | 2500:1 |
| 1.2 × 10$^5$ | 169,000 | 23:1 | 19,700 | 1600:1 |
| 1.4 × 10$^4$ | 27,000 | 3.6:1 | 1,300 | 11:1 |

As can be seen from these data, the lower detection limit in this case is less than 10$^4$ cells (a Signal/Noise ratio of 3:1 was chosen as the lower limit). The elution/recapture step advantageously increased the sensitivity of this particular assay by a factor of three (3).

7) Alternative assay formats

Evidence presented in Section 2 demonstrates that the basis of $GT^3$ hyperhybridization is RNA co-precipitation. With such a nonspecific labeling scheme, there is a potential for high background levels in assays. To obviate this difficulty, a modification is ideally made in the assay protocol to provide an opportunity for complementary molecules to specifically and selectively hybridize before they precipitate non-specifically. The altered format, which is hereafter referred to as Format II, is as follows:

a) Two microliters of target extracts (and competitor) were mixed with 100 ul of GuSCN solution containing 10% Dextran Sulfate.

b) Capture probe was added (to a final concentration of 0.2 ug/ml) and the mixture was vortexed; then the 3'-riboprobe was immediately added (final concentration 0.5 ug/ml) and the mixture was again vortexed, The resulting mixture was incubated at 37° C. for 2–3 minutes.

c) An equal volume (100 ul) of TMA.TFA/5% dextran sulfate solution (pre-warmed to 37° C.) was added, and the mixture thoroughly mixed and incubated at 37° C. for 15 minutes.

d) Prewarmed beads (200 ul) were added, and the mixture was vortexed and incubated at 37° C. for 6 minutes to effect capture.

e) The beads were separated magnetically and washed twice with 0.5M GuSCN wash buffer. (In some cases, the beads were counted to determine the amount of cpm's captured at this first round.)

f) Targets were chemically eluted by incubating for 3 minutes at 37° C. with 100 ul of 2.5M GuSCN.

g) The eluant was separated and transferred to new tubes. New beads were added and the mixture was incubated for 3 minutes at 37° C.

h) The beads were separated, washed twice with 0.5M GuSCN wash buffer and counted.

The following (Table 8) are typical results from experiments using Format II. *Listeria monocytogenes* or *Campylobacter jejuni* extracts were used as targets at a .concentration of $5 \times 10^5$ cells/ml, and *E. coli* was present at $2.6 \times 10^7$ cells/ml as a competitor. A control reaction contained *E. coli* but no true target extracts. Capture probes used in these experiments were: dA-795 capture probe for Listeria and dA-732 for Campylobacter.

TABLE 8

Assay performance using "Format II"

| Sample | Capture Round | Signal cpm | Riboprobes per cell | E. coli cpm | S/N |
|---|---|---|---|---|---|
| Listeria | 1 | 372,000 | 747,000 | 3,400 | 220:1 |
|  | 2 | 302,000 | 605,000 | 130 | 2,400:1 |
| Campylobacter | 1 | 422,000 | 847,000 | 51,000 | 8:1 |
|  | 2 | 211,000 | 423,000 | 2,700 | 77:1 |

As with other formats, assays with both Listeria and Campylobacter demonstrated "hyperhybridization" by their exceedingly high riboprobe to cell number. *E. coli* gave fairly high backgrounds with probe 732 (see U.S. Ser. No. 216,679 for further details) after the first capture round in this assay, but most of the noise was eliminated by means of a chemical elution followed by a second capture.

The same format was tested with *Neisseria gonorrhoeae* extracts ($5 \times 10^5$ cells/ml) while extracts from the close relative, *Neisseria meningitidis,* served as the control. In this experiment, the riboprobe concentration was lowered to 0.2 ug/ml final concentration but still the format resulted in the capture of an extremely high number of riboprobes/cell, indicating "hyperhybridization".

The following formats address the issue of increasing the assay specificity with reagents such as $GT^3$, which can otherwise cause nonspecific labeling. One potential problem with a nonspecific labeling scheme is that the specificity of the assay depends solely on the specificity of the single oligonucleotide capture probe. In many cases this does indeed provide sufficient specificity. For example, in the above Neisseria Format II experiment, hyperhybridization is sufficiently specific to distinguish *N. gonorrhoeae* from its closest relative, *N. meningitidis*. The 28-mer capture probe employed in that experiment had only 4 nucleotide mismatches with *N. moningitidis*, of which 2 were G:T basepairs. In essence, then, there were effectively only two strong mismatches; yet the assay readily distinguished them. This was due to the highly specific hybridization obtained in $GT^3$ of the *N. gonorrhoeae*-specific oligonucleotide to its target in $GT^3$. Data will also be presented below (Tables 10 and 11) demonstrating that $10^2$ *N. gonorrhoeae* cells were detected using hybridization with only one specific oligonucleotide in $GT^3$ in the presence of a 10,000- or 100,000-fold excess of *N. meningitidis*.

One advantage of sandwich-type assays such as reversible target capture is that the specificity is determined by the specificity of at least two probes. In some cases, such specificity may be necessary. One skilled in the art will realize that the following format, to be termed Format III, provides methods whereby such a highly desired level of specificity can be achieved.

Format III a) Hybridize a first specific oligonucleotide capture probe to a target in a suitable (nonprecipitating) reagent.

b) Capture on a first solid support.

c) Elute and rehybridize a second specific oligonucleotide capture probe (containing a second mixed-base sequence distinct from the mixed base sequence of the first probe) to the target.

d) Capture the target:probe complex on a second solid support via the second specific capture probe.

e) Elute the target:probe complex from the second solid support.

f) Add a suitable labeled probe and the reagents necessary to effect superstoichiometric labeling.

g) Use further cycles of release/recapture to reduce any nonspecific backgrounds as necessary.

h) Detect labeled targets

The following comments apply to this format:

a) The repetition of capture/release cycles lends itself most naturally to an automated assay.

b) The most preferred reagents of the present invention for hybridization to the target would be those possessing as many as possible of the desirable properties listed in the Summary of the Invention (above), except the ability to effect superstoichiometric labeling. (Precipitation of heterologous RNA and other cellular components would not be desirable in steps 1–4.)

c) The capture probes and the solid supports would preferably possess complementary members of affinity pairs. The affinity pairs employed in the first and second captures can be the same or similar in nature, or different in composition.

The following are examples of uses of a Format III assay.

1) Using the same or similar affinity pairs for the two captures

Both capture probes are ideally dA-tailed. The hybrid between the mixed-base sequence of the first capture probe and the target is advantageously less stable than that between the dA-tail and the oligo dT or poly-dT on the support. Thus, elution of the target from the support can be carried out without separating the first capture probe from the solid support. In addition, the mixed-base sequence of the second capture probe binds to the target to form a hybrid which is more stable than the hybrid between the dA-tail of this probe and the oligo-dT on the support. This enables the target to be repeatedly recaptured via the second oligonucleotide probe for reduction of nonspecific background.

One skilled in the art will realize that substantial differences in the lengths of the relevant mixed-base sequence and homopolymer sequences can be exploited to accomplish this. For example, one could use a short first mixed-base sequence and a long poly-dT on the first solid support, and a long mixed-base sequence on the second capture probe and a short oligo-dT on the second solid support.

The present invention provides additional, useful, and novel methods: tetraalkylammonium salts preferentially stabilize poly-dA:poly-dT base-pair bonds. Poly-dA:poly-dT, for example, has a $T_d$ of about 65° C. in 2.4M TEA.Cl, while a 35-mer mixed-base sequence has a $T_d$ of approximately 43°–44° C., regardless of GC content (Woods et al. (1985) Proc. Natl. Acad. Sci. USA, 82, 1585–1588). In the present example, this preferential strengthening of poly-dA:oligo-dT or poly-dA:poly-dT by tetraalkylammonium salts can be exploited to enhance the retention of the first capture probe on the first solid support during the elution of the target.

It is worth noting that this preferential stabilization of poly-dT:poly-dA by tetraalkylammonium cations can also be readily exploited in a useful generic stringency wash procedure with a target immobilized via poly-dT:poly-dA bonds. For a fixed oligonucleotide probe length, mismatched mixed-base sequences (pseudo-targets) can readily be removed from the solid support in a manner independent of GC content (i.e., with a single set of wash conditions) without any loss of genuine target from the support; this is accomplished by incubation just below the $T_d$ of the true target-probe hybrid.

2) Using different affinity pairs for the two captures

The first capture probe can be derivatized with biotin and the first solid support derivitized with streptavidin. The second capture probe is then advantageously dA-tailed and the second solid support coated with oligo-dT. In this case, both capture probes could be added in the first step of the assay, and the first elution could remove the target with or without the first capture probe.

One skilled in the art will readily realize that the affinity pairs could also be reversed: poly-dA:oligo-dT for the first capture and biotin:streptavidin for the second. (Additional dA-tailed capture probe can be added after the second elution if necessary.) The reversibility of the poly-dA:oligo-dT interaction could then be used to reduce the nonspecific binding of labeled probe to the support in subsequent steps.

One skilled in the art will further realize that the above methods and the reagents of the instant invention can be advantageously combined in numerous ways to gain even more specificity (for example, using three or more oligonucleotides). Furthermore, other affinity pairs such as antibody:antigen pairs, and/or any other pairs, may confer even greater specificity in the practice of the present invention, which employs a nonspecific labeling reaction with a generic labeled probe in the preferred method. Indeed such other methods of derivitizing and providing for specific ligand-ligand binding partner interactions become self-evident.

8) Dose-Response:*Neisseria gonorrhoeae*

The sensitivity of the assay (Format II) was examined using *N. gonorrhoeae* at $10^5$ to $10^2$ cells/ml; *N. meningitidis* was present in all assays at $5\times10^5$ cells/ml.

After a second capture, *N. gonorrhoeae* could be clearly seen above background at as low as $10^2$ cells/ml. (The S/N ratio was 3/1 or 7/1, for *Neisseria meningitidis* and *E. coli* control organism, respectively.) The level of hyperhybridization observed with $10^2$ cells/ml was almost 8 million probes per cell, which corresponds to nearly 800 probes per target.

A repeat experiment was performed using only 0.05 ug/ml riboprobe and the *N. meningitidis* competitor was increased to $10^7$ cells/ml. Targets were captured/recaptured three times.

Despite using only ¼ the previous amount of riboprobe, *N. gonorrhoeae* at $10^2$ cells/ml still could be seen above elevated competitor levels (S/N approximately 6:1).

The signals at $10^2$ *N. gonorrhoeae*/ml were comparable to those at $10^3$/ml, and both were well above backgrounds. While not wishing to be bound thereby, the explanation for this would seem to be that there are far more riboprobes captured per cell as the ratio of added labeled probes to target molecules increases. We have discovered that this unexpected phenomenon is useful since the need for greater signals is most critical at low target concentrations. Hyperhybridization with the instant reagent thus promotes this enhancement precisely where it is most needed.

9) Dextran Sulfate not necessary for hyperhybridization

Since "hyperhybridization" appears to be a precipitation phenomenon, the assays were performed in the presence of 0%, 2%, 4%, 6%, 8% and 10% (mass/volume) dextran sulfate (A stock {65%, mass/volume} solution was prepared by, e.g., dissolving 65 g Dextron Sulfate in buffered water, and adjusting the final volume to 100 mL: the result was a "65%" solution. An appropriate volume of this stock was added to each reaction mixture to give a final concentration as desired {2%–10%}.) using Listeria as a model to determine whether dextran sulfate was necessary with $GT^3$. These experiments showed that dextran sulfate had no appreciable affect on the signal. The average signal was approximately 250,000–300,000 riboprobes/cell with an average *E. coli* S/N of 500:1 after a second capture (the target cell concentration was $10^5$ cells/ml).

10) Concentration of Riboprobe

An experiment was done to compare how much riboprobe could be used to adequately detect a number of target levels in $GT^3$ versus GuSCN. Again, *N. gonorrhoeae* was used at $10^5$ and $10^4$ cells/ml, with 0.2 ug/ml capture probe, and riboprobe concentrations of 0.2 ug/ml, 0.05 ug/ml and 0.0125 ug/ml. *N. mengitidis* was present as a competitor at $5\times10^5$ cells per assay. Two rounds of capture were performed. The results indicated that as little as 12.5 ng/ml riboprobe was sufficient to detect target at well above competitor background. This was some forty-fold less than the concentration required for efficient labeling In GuSCN, where the mechanism of labeling is classical hybridization. A considerable savings in assay cost is thus an added and unexpected advantage of hyperhybridization in $GT^3$.

F. Reporter probes:Riboprobes vs. oligonucleotides

It was further discovered that the observed "hyperhybridization" phenomenon in $GT^3$ generally correlates with the presence of a Riboprobe of either the 3'- or 5'- variety. This is useful to recognize since in some instances, in order to increase the selectivity of an assay, it may be desirable to use a target-specific reporter-oligomer (in combination with a specific capture probe) rather than a generic rRNA Riboprobe. In such instances since superstoichiometric labeling generally occurs only if the labeled probe is a Riboprobe, the preferred way to increase selectivity is to develop an assay format using two specific capture probes and subsequently a nonspecific labeling reaction with a Riboprobe.

G. RNA:DNA Hybrid melting

A nucleic acid melting curve reveals important information about a reagent and the hybrids formed therein. Specifically, it indicates whether a true hybrid is present (if so, it will have a clear melting point) and whether or not GC and AT base-pairs are equally strong if they are, the melting curve will be sharp, and the melting/dissociation temperatures ($T_d$'s) of various hybrids of the same length but different GC/AT content will be nearly equal.

$GT^3$ melting experiments were conducted with a variety of target rRNA's, reporter probes and capture probes, as listed in the following table.

TABLE 9

Target/probe combinations used in melting studies

| Target rRNA | Labeled (reporter) probe | Tailed (capture) probe |
| --- | --- | --- |
| Campylobacter | Riboprobe | dA-732 |
| E. coli | Riboprobe | dA-787 |
| Salmonella | Riboprobe | dA-676 |

Hybrids were formed in $GT^3$ by overnight incubation at 37° C. with target cell extracts at $10^7$–$10^8$ cells/ml, reporter probe at 1 ug/ml and capture probe at 0.25 ug/ml. This hybridization mixture was then diluted by 1/10 with $GT^3$ and held at 37° C. for the course of the melting experiment.

Aliquots were removed periodically and incubated at various elevated temperatures for six minutes, after which the intact S complexes were captured on magnetic beads, washed and counted as described in section 1.A. As a control, periodically over the course of the experiment aliquots held at 37° C. were subjected to the capture procedure to monitor any changes in the level of hybridization over time. The number of intact (i.e., captured) hybrids at each elevated temperature, relative to the number of intact hybrids in the 37° C. control tube, was calculated.

Table 10 presents results from these experiments.

TABLE 10

Melting of various target/probe complexes using a $^{32}$P-Riboprobe as reporter (from FIG. 6)

| Target rRNA | Capture Probe | GC content of probe | $T_d$ | Width* ($\Delta T^{3/4} - 1/4$) |
| --- | --- | --- | --- | --- |
| Campylobacter | dA-732 | 46% | 51–52° C. | ≦5° C. |
| E. coli | dA-787 | 37% | 48° C. | ≦5° C. |

TABLE 10-continued

Melting of various target/probe complexes using a $^{32}$P-Riboprobe as reporter (from FIG. 6)

| Target rRNA | Capture Probe | GC content of probe | $T_d$ | Width* ($\Delta T^{3/4} - 1/4$) |
| --- | --- | --- | --- | --- |
| Salmonella | dA-676 | 43% | 49° C. | ≦7° C. |

*Curve width is, by standard definition, the temperature range over which one observes a transition from 3/4 of the hybrids being intact to 1/4 being intact. The actual widths are suspected to be equal to or less than those reported in this table because the temperature-points used in the experiment were 5° C. apart: by sampling more frequently one can generally obtain sharper curves.

As can be seen, the $T_d$'s are within 3°–4° C. of each other and the melting curves have widths ($\Delta T^{+hd}$ 3/4 $^{+hd}$ 1/4) of 5°–7° C. These widths are comparable in size to the spacing of the data points (5° C.). These results can be compared to our results obtained in 3.0M TMACl where the $\Delta T^{+hd}$ 3/4 $^{+hd}$ 1/4 was 6°–8° C. TMACl is a reported GC/AT equalizer (Melchior and von Hippel, PNAS 70 (1973), 298–302). The similarity of the dissociation temperatures indicates that the desired effect of GC/AT equivalence was obtained.

H. DNA:DNA melting in GuSCN:TMA.TFA combination reagents

In section 1.G the data associated with DNA:RNA melting in $GT^3$ were sharp indicating good specificity of base-pairing and a reasonable degree of GC/AT equivalence. This can also be demonstrated with a DNA:DNA oligomer:oligomer system (one oligomer radio-labeled, the other one dA-tailed for bead-capture) and because of its greater simplicity (compared to the system containing a reporter probe (labeled Riboprobe or oligomer), a capture probe, a target RNA and the assorted components from cell extracts), such a system is more easily interpreted. Additionally, using oligomers, one can choose almost any sequence, with a wide range of GC-content, for the experiments. In this section, melting experiments were carried out with such a DNA:DNA system as described.

The basic protocol for these experiments was the same as that described in section 1.G. In $GT^3$, hybridization was accomplished by incubation at 37° C. Hybridization in GuSCN was advantageously carried out at room temperature, as the relatively low hybrid melting temperature was found to contraindicate 37° C. incubation. In the hybridization mixture, the $^{32}$P-labeled oligomer was present at 50 ng/ml, and the dA-tailed capture probe at 100 ng/ml. Hybridization was found to occur rather rapidly (reaching a plateau within 5 minutes in one case), and the hybrids were stable at the incubation temperature for at least two days; hybrids formed in this way could be used in melting experiments after a short incubation or after a day or two of incubation. Initially, the hybridization mixture was diluted 10-fold prior to carrying out melting experiments; after the protocol, a 40-fold dilution was discovered to be optimal.

Two pairs of oligomers were used for the melting experiments. Of each pair, one oligomer (the target) was 5'-$^{32}$P-labeled and the other (the capture probe) was dA-tailed. The sequences of the target probes were E. coli rRNA sequences, and the capture probe sequences were complementary thereto.

All oligomers were 35 nucleotides in length. The two pairs were chosen to represent sequences of minimal and maximal GC-content. The oligomers chosen were as follows:

| Target oligomer | Capture probe | GC-content |
| --- | --- | --- |
| #855 | $dA_{112}$-730 | 37% |
| #853 | $dA_{125}$-854 | 66% |

The following dissociation temperatures ($T_d$'s) were calculated from the melting curves obtained with these two pairs of oligomers in 2.5M GuSCN and $GT^3$:

TABLE 11

| Dissociation Temperatures of DNA:DNA Hybrids | | |
| --- | --- | --- |
| GC-content | in GuSCN | in $GT^3$ |
| 37% | 39° C. | 49° C. |
| 66% | 54° C. | 57° C. |

These data indicate that $GT^3$ is nearly twice as effective a GC/AT-equalizing reagent than is GuSCN: in the former the difference in the $T_d$'s of the two pairs of oligomers was 8° C., while in the latter it was 15° C. It was also discovered that in $GT^3$ the DNA:DNA dissociation temperatures were quite similar to DNA:RNA $T_d$'s which unexpectedly makes the reagent especially useful for the standardization of instrument-based assays, particularly if such have the capability of doing either DNA:DNA or DNA:RNA hybridization assays. The low $T_d$ (39° C.) of a 37%-GC 35-base-pair DNA:DNA hybrid in GuSCN should also be noted: this indicated that there would be a problem hybridizing low-%-GC sequences of 35 or fewer nucleotides at 37° C. in GuSCN, and thus further points to the utility and advantage of the present reagents in equalizing the GC/AT base-pairs.

A 40:60 mixture of 5M GuSCN and ⁻4M TMA.TFA was tried to further reduce the difference in the $T_d$'s. (In the present document this mixture will be referred to as 40:60 $GT^3$, or simply as $GT^{3*}$; it is another member of the $GT^3$ family.) Melting experiments were carried out in this reagent (protocol as above), and from the results the $T_d$'s were calculated and are listed below.

TABLE 12

| Dissociation Temperatures of DNA:DNA Hybrids | | |
| --- | --- | --- |
| GC-content | in GuSCN | in $GT^{3*}$ |
| 37% | 39° C. | 52° C. |
| 66% | 53° C. | 58° C. |

As these numbers indicate, 40:60 $GT^3$ is a still more preferred GC/AT equalizer than 50:50 $GT^3$. The difference in $T_d$'s of the two oligomer pairs is 6° C. in the former, compared to 8° C. in the latter. A comparison of the data revealed that the decrease in the difference was apparently due primarily to the strengthening of the AT base-pairs, since the $T_d$ of the AT-rich oligomers changed more than that of the GC-rich oligomers.

The following experiments tested the 40:60 $GT^3$'s ability to promote hybridization and inhibit RNase.

I. 40:60 $GT^3$:Signal and Noise, and RNase inhibition

Using Campylobacter extracts as a target, and *E. coli* extracts as a control, the level of hybridization in 40:60 $GT^3$ was shown to be 3–5-fold higher than in 50:50 $GT^3$. The noise level increased by the same amount, so the Signal/Noise ratio remained constant thereby indicating no further hybridization enhancement.

Next, an RNase A inhibition experiment was carried out as described in section 1.D. Pre-formed hybrids were diluted into 0.1M Phosphate (pH 7.55), 2.5M GuSCN, $GT^3$ (50:50) or $GT^{3*}$ (40:60). After incubation in the presence of various concentrations of RNase A, intact targets were captured on magnetic beads and the fraction of intact targets (relative to a no-RNase control) was determined. The results are presented in FIG. 6. In this figure, the fraction of intact targets, which is proportional to the level of RNase inhibition, is presented as a function of RNase A concentration. Clearly $GT^{3*}$ and $GT^3$ effectively inhibit RNase A. Thus, decreasing the fraction of GuSCN in the combination reagent from 50% to 40% advantageously provided no adverse effect in terms of nuclease protection.

J. Cellular lysis

A series of experiments was performed to assess the ability of the new reagent to lyse bacterial cells. The lysis capabilities of the new reagents were compared to those of SDS/Proteinase K and/or Guanidinium Thiocyanate, both of which had been shown to be useful as lysing agents. The standard method for determining the extent of lysis is to determine the relative decrease in the optical density (O.D.) at 550 nm of an aliquot of cells after a 15 minute incubation in the medium of interest at a specified temperature. We used *E. coli* and four Salmonella species (brookfield, bulawayo, minneapolis, typhimurium) as the target cells in our studies.

As noted earlier, in a typical experiment SDS (0.5%) plus Proteinase K (0.5–1.0 mg/ml) lysed (5–10 minutes at 55°–65° C.) 90–100% of an aliquot of cells. GuSCN (2.5M) plus Sarkosyl (0.5%) typically lysed (15 minutes at 37° C.) 75–95% of the target bacterial cells; the addition of Proteinase K to this lysis cocktail was found not to increase the extent of lysis.

Lysis experiments were carried out with $GT^3$ (a 1:1 mixture of 5M GuSCN (buffered with Tris/EDTA) and 4M TMA.TFA (buffered with 100 mM phosphate, 100 mM borate and 50 mM EDTA)) and $GT^5$ (a 1:1:1 combination of 5M GuSCN, 4M TMA.TFA and 4M TMA.SCN (buffered as TMA.TFA was)) and various combinations of additives: DTT (0.5%), Sarkosyl (0.5%), Proteinase K (0.5 mg/ml). Incubation was at 37° C. or 65° C. The data obtained with each tested combination of additives and the five bacterial species mentioned above were averaged. Since there was no significant difference in lysis as a function of temperature the data obtained at both temperatures were analyzed together. The results are summarized in Table 13.

TABLE 13

| Extent of cellular lysis in $GT^3$ and $GT^5$ | | |
| --- | --- | --- |
| | Extent of Lysis | |
| Additive | $GT^3$ | $GT^5$ |
| none | 47% ± 2% | 43% ± 3% |
| Sarkosyl | 66% ± 3% | 63% ± 2% |
| Sark., DTT | 78% ± 4% | 73% ± 5% |
| Sark., PK | 85% ± 3% | 89% ± 3% |

Under "Extent of Lysis," the uncertainties (±) are Standard Errors of the data.

From these data, it became apparent that the lysis efficiency of either $GT^3$ or $GT^5$ could be improved by the addition of any combination of the additives listed with the Sarkosyl/Proteinase K combination being most preferred.

An alternative approach to the development of an assay with $GT^3$ as the hybridization medium, is to first lyse the target cells with GuSCN, SDS or Proteinase K, which will result in a very good overall detection efficiency.

K. Assay performance with a biological specimen

The experiments reported above all involved the detection of targets from bacterial cell extracts. To evaluate the performance of GT³ under more 'real' conditions, an experiment to detect targets in nonfat dry milk (NFDM) was performed. The protocol was as follows.

NFDM was dissolved in 5M GuSCN (plus 1% Sarkosyl and 10% by weight dextran sulfate) to a final concentration of 10% (w/v). One volume of this solution was then combined with one volume of 4M TMA.TFA (plus 7% by weight dextran sulfate). The resulting solution was "GT³" with 5% NFDM, 0.5% Sarkosyl and 8.5% dextran sulfate: hereafter referred to as "NFDM/GT³." To this mixture Listeria extracts (experimental target) were added to a final concentration of $5\times10^5$ cells/ml, or *E. coli* extracts (negative control) to a final concentration of $10^8$ cells/ml. As a positive control, Listeria extracts were added to GT³ (with dextran sulfate and Sarkosyl) to a final concentration of $5\times10^5$ cells/ml. A Listeria-specific capture probe (dA-tailed #795) was added to all samples at 0.2 ug/ml, and a $^{32}$P-labeled 3'-Riboprobe at 0 5 ug/ml. After a 15-minute incubation at 37° C. one volume of magnetic beads was added and the samples were incubated at 37° C. for 6 minutes. Beads were washed three times, after which the samples were eluted in 2.5M GuSCN and then recaptured by the addition of two volumes of beads. The beads were washed twice and counted. The results were as follows:

TABLE 14

Hybridization in Nonfat Dry Milk in GT³

|  | Listeria in GT³ | Listeria in NFDM/GT³ | E. coli in NFDM/GT³ | | |
|---|---|---|---|---|---|
|  | R' probes per cell | R' probes per cell | cpm (S) | cpm (N) | S/N |
| Bead-bound, first round | 541,000 | 258,000 | 311,000 | 14,100 | 22:1 |
| Eluted | 448,000 | 224,000 | 258,000 | 6,600 | 39:1 |
| Bead-bound, second round | 384,000 | 143,000 | 221,000 | 23 | 9,600:1 |

From these data it was apparent that:

1) The differences in labeled probes captured per cell in GT³ and NFDM/GT³ indicate that there was some competition for the labeled probes in NFDM. (In a similar experiment where the Riboprobe was bound to targets only after a preliminary round of target capture to remove competitors, there was no signal reduction due to competitors in NFDM.)

2) Even in the presence of NFDM, the extent of hyperhybridization was still very great: after two rounds of capture, 143,000 probes were bound per cell (compared to 384,000 without NFDM).

3) The background levels were low after two rounds of capture: in the presence of NFDM, the S/N ratio was nearly 10,000:1 (with only $10^5$ cells in the sample). This sensitivity is far more than adequate to detect contaminating bacteria in foods since a typical food sample contaminated with only one Listeria cell gives rise to at least $10^6$ cells/ml after standard (BAM/AOAC) cultural enrichment.

4) Additional assay steps, such as a final filter capture, may advantageously enhance the sensitivity even further.

L. A GT³ Elution Buffer

The designation "GT³" refers not to a single reagent but to a family of reagents containing GuSCN, TMA.TFA and buffers, combined in various ratios. When the combination ratio is not specified, it is understood to be 1:1, referring to the medium in which most of the experiments described herein were done. However, variations on this basic reagent have been prepared and have been shown to have properties similar to those of the basic reagent. Examples of such preferred variants are: 40:60 GT³ (GT³*) and GT⁵. The former of these was more preferred since it conferred a greater degree of GC/AT equivalence on hybrids than did the 1:1 reagent.

One variant which has been shown to have desirable properties for a special application is an elution buffer comprising mostly GuSCN (the main component of the standard chemical elution buffer), with a small amount of TMA.TFA added. To evaluate this buffer, the following experiment was carried out. In GT³, hybrids were formed involving a $^{32}$P-labeled Riboprobe, a dA-tailed capture probe, and rRNA from extracts (at $5\times10^5$ cells/ml) of *Salmonella typhimurium* and *Neisseria gonorrhoeae*. With the Salmonella capture probe a control experiment was run with extracts from *E. coli* ($5\times10^7$/ml), while with the *N. gonorrhoeae* probe a control was run with *N. meningitidis* extracts. After hybridization, the macromolecular complexes were captured on magnetic beads, and the beads were washed once with 0.5M GuSCN Wash Buffer (at room temperature), once with 2.0M GuSCN Wash Buffer (for 2 minutes at 37° C.), and one final time with 0.5M GuSCN Wash Buffer (room temperature). Elution buffer (of various compositions, as listed below; prewarmed to 37° C.) was then added to the beads and incubated at 37° C. for 2 minutes, after which the eluate was transferred to a clean tube. The Elution Buffers used were as indicated in the following table.

| Designation | GuSCN | TMA.TFA |
|---|---|---|
| A | 3.3M | — |
| B | 3.1M | 0.2M |
| C | 3.0M | 0.4M |
| D | 2.6M | 0.8M |

The eluted complexes were then recaptured on magnetic beads, and the beads were washed three times with 0.5M GuSCN Wash Buffer (at room temperature) and counted in a scintillation counter.

The results of this series of experiments are presented in Table 15.

TABLE 15

Elution in GuSCN and "GT³-type" buffers

| Target | Elution Buffer | Signal (cpm) 1st capture | Signal (cpm) 2nd capture | Control (cpm) 1st capture | Control (cpm) 2nd capture |
|---|---|---|---|---|---|
| *Neisseria gonorrhoeae* | A | 318,000 | 13,100 | 8,300 | 690 |
|  | B | 321,000 | 88,700 | 7,700 | 140 |
|  | C | 338,000 | 133,000 | 7,100 | 420 |
|  | D | 327,000 | 61,000 | 6,600 | 680 |
| Salmonella | A | 223,000 | 2,920 | 3,100 | 34 |
|  | B | 218,000 | 21,700 | 6,300 | 150 |
|  | C | 229,000 | 63,400 | 2,400 | 84 |
|  | D | 248,000 | 89,900 | 4,200 | 170 |

From these data it can be seen that the addition of a small amount of TMA.TFA (to a final concentration of 0.2–0.4M) to the elution buffer advantageously enhances the post-elution recapture in both cases, though to different extents depending on the target. Background levels did not increase to the same extent as signals thereby increasing the S/N levels.

It was thus discovered that a GuSCN elution buffer with a small amount of TMA.TFA has the capability of advantageously improving assay performance by improving post-elution recapture on magnetic beads. A hypothetical explanation for this is that the TMA.TFA, even at low concentrations, prevents the hyperhybrids (precipitates: see below) from disaggregating, thus minimizing signal loss through the elution/recapture process. Those skilled in the art will now recognize that by optimizing the precise composition of the elution buffer one can maximize both signal preservation and noise reduction.

II. Mechanism

In the course of experiments with the new reagents of the present invention, the observation was made that a substantial precipitation occurred upon the addition of 4M TMA.TFA to concentrated ($>10^{10}$ *E. coli*/ml) cell extracts in 5M GuSCN. The precipitate formed was large enough to settle out of solution under the force of gravity. Since $GT^3$ is a 1:1 mixture of 4M TMA TFA and 5M GuSCN, the nature of this precipitate and its possible role in hyperhybridization in $GT^3$ was questioned. The formation in $GT^3$ of a precipitate, comprised of the target molecule as yell as the hybridized capture probe and a large number of labeled riboprobes, would be a possible explanation for the phenomenon of hyperhybridization, in which a very high number of riboprobes are detected per target molecule. If precipitation does play a role in hyperhybridization, it is important to fully understand its nature in order to control it, to enhance it, and in certain cases to make it selective. It was surprisingly discovered that indeed, with the reagents of the present invention, the selectivity of the precipitation can be controlled, thereby allowing for the development of a very rapid RNA isolation procedure.

A number of experiments were performed to define the nature of the precipitate including measuring the amount and type (eg dsRNA, ssRNA, cDNA, etc) of nucleic acids which precipitated in $GT^3$, nucleic acid precipitation at various temperatures and at various cell concentrations, and whether the precipitate could be dissolved and re-precipitated. It was surprisingly discovered that little difference was seen in the precipitation of the riboprobe (ssRNA) on ice, at room temperature, at 37° C., or at 65° C., indicating that hyperhybrids will probably be stable even at 65° C. in $GT^3$. The precipitation of the dsDNA was fairly constant at the three lower temperatures, but did show a sharp decrease at 65° C. The differential stability of dsDNA and the riboprobe would ideally be exploited as follows: backgrounds (resulting from the presence of dsDNA) are ideally removed from true hybrids (containing riboprobes) by carrying out a $GT^3$ stringency wash at a temperature a few degrees below the hybrids' $T_d$ in $GT^3$ (53°–58° C.).

It was also discovered that oligomers do not precipitate at the same levels as riboprobes. This demonstrates why riboprobes are preferred as reporter probes (as opposed to oligonucleotides) in order to advantageously obtain hyperhybridization.

The precipitation of dsDNA appeared to be efficient only et very high cell concentrations and surprisingly was inhibited by the presence of dextran sulfate. This distinction can thus be advantageously exploited in an RNA isolation procedure, and/or a nucleic acid probe assay wherein the target is RNA.

The experiments also demonstrated that the absolute amount of nucleic acid precipitated by $GT^3$ varied somewhat from experiment to experiment correlating with the variability of the amount of hyperhybridization from experiment to experiment.

A. Dissolution and Re-recipitation of $GT^3$ Precipitates

In order to fully detect hyperhybridization non-isotopically in a generic assay format, it may be necessary to dissolve the "hyperhybrid" prior to the detection step of the assay. Experiments to further explore the hyperhybridization phenomenon demonstrated that 2.4M TEA.Cl does indeed dissolve hyperhybridization complexes. The $GT^3$ precipitation assay described above was used to examine the resuspension of precipitated nucleic acids, using 2.4M TEA Cl, thermal elution buffer (containing 0.5M NaCl), and 5M GuSCN. Results showed that both precipitated ssRNA and dsDNA were efficiently resuspended in all three solutions. Resuspension in 5M GuSCN has the advantage of making possible the subsequent re-precipitation of the nucleic acid by the addition of 4M TMA.TFA. This would be of special advantage in gaining additional purity in an isolation procedure. The phenomenon can also be used in a nucleic acid probe assay to lessen the trapping of oligomeric capture probes in precipitates and indeed, hyperhybridization complexes can be dissolved with thermal elution buffer and with 5M GuSCN, as well as with 2.4M TEA.Cl. It has also been discovered that 2.4M TEA.Cl disrupted "hyperhybrids" formed in $GT^3$. Virtually all signal was lost as a result of TEA.Cl-washing. Control experiments showed that the oligonucleotide-target bond and the capture probe-bead bonds were stable to TEA.Cl-washing. Accordingly, once dissolved with 5M GuSCN, such complexes can be reformed upon the addition of 4M TMA.TFA.

B. Hyperhybridization with a ss-DNA Target

One also can advantageously apply hyperhybridization to ss DNA targets, as in the following scheme. First, one hybridizes a target to a specific oligonucleotide probe; the probe also has a tail which is complementary to a subsequently added, labeled riboprobe. Next, one adds the labeled complementary riboprobe. This converts the ss-DNA target, which is not precipitable, to a complex containing ss-DNA linked to a large ss-RNA through the oligonucleotide probe. This ss-DNA:ss-RNA complex is significantly different from a DNA:RNA hybrid (which does not precipitate as well in $GT^3$), and thus it precipitates in $GT^3$ by virtue of its large single-stranded RNA moiety. The advantages of this method are that (1) it makes it possible to effect superstoichiometric labeling with ss-DNA targets, and (2) it makes it possible to use generic labeled riboprobes with non-complementary target sequences.

C. Summary: Mechanism of Hyperhybridization

Single-stranded (ss) and double-stranded (ds) RNA were shown to precipitate well in $GT^3$, while oligonucleotides, ssDNA and RNA:DNA hybrids remained soluble. Double-stranded DNA precipitated well only at high cell concentrations (suggesting that it was merely being non-specifically trapped), and its precipitation was inhibited by high temperatures and dextran sulfate. These experiments indicated that precipitation of ssRNA can explain hyperhybridization. For example, oligomers are soluble in $GT^3$, while riboprobes are not. This explains why hyperhybridization was observed with riboprobes but not with oligomers. It also accounts for the specificity of the hyperhybridization phenomenon: the only way a tailed oligonucleotide becomes associated with the precipitated RNA-target:RNA-probe complex is via hybridization (except for a small amount of non-specific trapping of the oligonucleotide in the precipitates. This trapping is ideally reduced by cycles of solubilizing and precipitating the RNA, or by the use of two or more cycles of capture/release with two or more specific oligomeric capture probes.) While precipitation may occur in the absence of hybridization of the capture probe, such background precipitates are not capturable.

Other pertinent correlations that were discovered include the following: TEA.Cl-washes disrupted hyperhybrids and also dissolved precipitated riboprobes, hyperhybrids were stable beyond 50° C. and the precipitated riboprobe was stable at 65° C. in *E. coli* extracts processed in $GT^3$.

Superstoichiometric labeling is preferably carried out in solution because of the preferred rapid kinetics of solution-phase reactions. However, those skilled in the art will realize that in principle the process should also occur with the target immobilized on a solid support (either directly, or indirectly through a capture probe). One skilled in the art will further realize that the kinetics of such a process may not be compatible with rapid diagnostic assays, but may be enhanced by the addition of an appropriate accelerator(s) such as, but not limited to, dextran sulfate.

Contrary to Kohne's explanation of accelerated hybridization (see Background) the uniqueness and significance of the novel reagents of the invention is that not only has the rate of hybridization been greatly enhanced, but so also has the magnitude of the hybridization signal, without a proportional increase in hybridization background.

Comparison of the Conventional Assays with the Preferred Methods using $GT^3$

An experiment was done to compare conventional hybridization in SET ("1x SET" consists of 150 mM NaCl, 1 mM EDTA, 10 mM Tris HCl, pH8.0) buffer on nitrocellulose filter membranes with the preferred embodiment of the present invention. *Listeria monocytogenes* cell extracts were diluted to various concentrations, spotted on nitrocellulose filters with a diluent-only spot as a control, and affixed by baking the membranes. All filters were prepared in duplicate. Hybridizations were then carried out following standard procedures (overnight incubation at 65°–68° C.), using a $^{32}$P-labeled Riboprobe as the reporter probe. The filters were then rinsed (as per standard protocols) and subjected to washes of various stringency levels (1.5x, 1.0x and 0.5x SET). After drying, the spots were cut out, dried and counted. Signal-to-noise ratios were calculated (the diluent-only spot was the "Noise"). The 0.5x SET stringency wash gave rise to the best S/N ratios, and data from these filters are presented in the following table:

| Filter Hybridizations in SET: Listeria Dose-Response | |
|---|---|
| Cells per spot | Signal/Noise Ratio |
| $1.5 \times 10^6$ | 136 |
| $4.7 \times 10^5$ | 30 |
| $1.5 \times 10^5$ | 8.3 |
| $4.7 \times 10^4$ | 1.5 |
| $1.5 \times 10^4$ | 0.6 |

Since a Signal/Noise ratio of 3 is ordinarily taken as the cut-off for detection sensitivity, these data indicate a sensitivity of $1.5 \times 10^5$ cells. A similar dose-response experiment was carried out using the preferred liquid-phase hybridization method in $GT^3$, followed by three rounds of reversible target capture, as previously described. The results were as follows:

| Solution Hybridizations in $GT^3$: Listeria Dose-Response | |
|---|---|
| Cells per assay | Signal/Noise Ratio |
| $1.5 \times 10^6$ | 1675 |
| $1.5 \times 10^5$ | 1237 |
| $1.5 \times 10^4$ | 553 |
| $1.5 \times 10^3$ | 52 |
| $1.5 \times 10^2$ | 3.5 |

In this experiment, the detection sensitivity was $1.5 \times 10^2$ cells showing an unexpected and tremendous improvement over conventional methods and reagents. In addition, these vastly superior results were obtained in approximately 1 hour while the conventional assay required 24 hours.

III. TMA.TFA:TMA.SCN("$T^3$")

Experiments carried out in TMA.TFA (Section V) demonstrated that with this reagent the rate of hybridization was extremely fast, but that melting curves were less advantageous or that elution was more difficult. In TMA. SCN, on the other hand, both melting and elution were more advantageous. To test whether the preferred properties of these two reagents could be combined, a series of experiments examined the melting characteristics of DNA:DNA hybrids in TMA.SCN (Section IV) and a mixture of TMA.TFA and TMA.SCN.

At the same time, a mixture of TMA.SCN and GuSCN was examined. In this mixture there were approximately equimolar amount of TMA (an "equalizing cation") and Guanidinium (not an "equalizer"), and twice as much chaotropic anion (SCN) as either cation alone.

The final ion concentrations were as listed below

| Reagent | TMA | Gu | SCN | TFA |
|---|---|---|---|---|
| A | 2.5M | — | 2.5M | — |
| B | 2.85M | — | 1.25M | 1.6M |
| C | 1.25M | 2.1M | 3.25M | — |

The hybridization in TMA.SCN/GuSCN (Reagent "C") was generally much less preferred. Preferred melting curves were obtained with the other reagents thereby demonstrating that the mixed salt (reagent "B", hereafter referred to as "TMA.TFA/SCN" or "$T^3$") conferred melting characteristics at least as advantageous as those observed in TMA.SCN alone.

Similar RNA:DNA melting experiments were conducted with $T^3$ following the general experimental protocol outlined in section 1.A. The final salt concentration was ~2.5M TMA, ~1.3M TFA, ~1.1M SCN. The resultant melting curve was clearly much sharper ($\Delta T^{+hd}$ ¾ ¼ =~-9° C.) than was obtained in TMA.TFA, and points to the preferred utility of this combination reagent for this purpose.

Hybridization kinetics were measured in $T^3$ relative to other reagents. The final salt concentrations of the reagents were as follows:

| Reagent Designation | Salt |
| --- | --- |
| E | 2.5$\underline{M}$ GuSCN |
| F | 2.6$\underline{M}$ TMA.TFA |
| G | 2.1$\underline{M}$ TMA.SCN |
| H | 2.4$\underline{M}$ TMA, 1.1$\underline{M}$ SCN, 1.3$\underline{M}$ TFA |

Results obtained in these experiments demonstrated that the best hybridization results were obtained in $T^3$. Though hybridization in TMA.TFA was initially faster than in TMA.SCN, the level of hybridization subsequently fluctuated. The hybridization properties of $T^3$ are advantageously superior to those of TMA.SCN (in terms of rate and level) and to those of TMA.TFA (in terms of rate, level and stability); and all were clearly and surprisingly superior to the hybridization properties of conventional GuSCN in terms of both rate of reaction and level of signal.

To test the specificity of hybridization in $T^3$, two control experiments were performed. In the first control, wherein the target was rRNA from *E. coli* extracts, the number of counts captured was 7.5% of the reference experiment. In the second control, with no capture probe, the signal level was 4.5% of the reference. These data reflect the advantageous ability of the reagent to effect minimal non-specific hybridization and little non-specific (non-hybrid) binding.

As just described, hybridization proceeded faster and to a greater extent in $T^3$ than in TMA.TFA. These results were obtained with one type of rRNA (from Salmonella extracts). To show that use of the novel reagents of the present invention was not limited to one rRNA species, a series of experiments was carried out using three different species of rRNA, three probe concentrations and the reagents of interest.

Reagent concentrations were: for TMA.TFA, 2.6M; for TMA.TFA/SCN, 3.4M TMA, 1.3M TFA, 2.1M SCN. From the resultant data the following conclusions obtain:

1) In all the extracts examined, at a probe concentration of 100–500 ng/ml, hybridization was faster in TMA.TFA/SCN than in TMA.TFA (on average, twice as fast in the first five minutes).

2) In all the extracts examined, at a probe concentration of 100–500 ng/ml, hybridization proceeded to a greater extent in TMA.TFA/SCN than in TMA.TFA (on average, 3 times as much after sixty minutes).

3) In TMA.TFA/SCN, a capture probe concentration of 100 ng/ml was just as good as a concentration of 500 ng/ml, in terms of both the rate and the extent of hybridization.

As noted above, one very desirable, but not essential, property in a hybridization reagent is the ability to inhibit Ribonuclease. Data from experiments showed that TMA.TFA/SCN inhibits RNase A at concentrations up to 0.125 ug/ml as well as, or better than, GuSCN. However, at higher RNase concentrations GuSCN was a better inhibitor of RNase A than was TMA.TFA/SCN.

Next, Proteinase K was added to the reagent mixture to see if it would remain sufficiently active to decrease the RNase activity. The results demonstrated that there was inhibition of the RNase activity by the Proteinase K in TMA.TFA/SCN. For example, with RNase at 1.25 ug/ml, in TMA.TFA/SCN, Proteinase K reduced RNase activity by approximately 20%.

A more direct test of Proteinase K's utility (examining its ability to digest BSA) also demonstrated that the protease was active in $T^3$. This was in agreement with earlier described results where it was observed that PK partially inhibited RNase A in $T^3$. In another experiment it was observed that 25–50% of the Proteinase K activity was lost when the enzyme was stored at 37° C. in $T^3$ over a period of two hours, while under similar circumstances in GuSCN, 80% of the enzymatic activity was lost.

A series of experiments was carried but to assess the ability of $T^3$ to lyse bacterial cells. The data showed that $T^3$ lysis efficiency could be advantageously enhanced by the addition of SDS and Proteinase K, or to a lesser extent SDS alone or SDS and DTT.

IV. TMA.SCN

Tetramethylammonium sulfate ($[TMA]_2.SO_4$) was prepared by neutralizing tetramethylammonium hydroxide with sulfuric acid. Tetramethylammonium thiocyanate (TMA.SCN) was prepared by combining equimolar amounts of $[TMA]_2.SO_4$ and barium thiocyanate in solution, forming TMA.SCN (which is soluble) and barium sulfate (an insoluble precipitate):

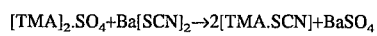

$$[TMA]_2.SO_4 + Ba[SCN]_2 \rightarrow 2[TMA.SCN] + BaSO_4$$

Free barium ions in solution can be detected using rhodizonic acid, which forms an easily detectable insoluble red salt with the cation. (Feigl, F., Spot Tests, vol. I (1954, Elsevier, Amsterdam); Vogel, A. I., Qualitative Inorganic Analysis (1979, Longman/Wiley, New York, N.Y.). This analytical test was used to determine the end-point of the reaction in the production of TMA.SCN: TMA.Sulfate was added to a solution of Ba[SCN]2, with periodic monitoring for Ba+, until the last of the barium had just precipitated from the solution. This was the equivalence point of the reaction, with resulting equal molar concentrations of TMA and thiocyanate, and with barium sulfate precipitated out of solution. The resulting mixture was centrifuged and the supernatant, which was a concentrated solution (approximately 6M) of TMA.SCN, was decanted. This solution was buffered (100 mM Phosphate, 100 mM Borate, 50 mM EDTA; brought to pH 7.5 with TMA.OH) and has been found to be quite stable.

The concentration of thiocyanate can be determined by any one of a variety of standard analytical techniques. Colorimetric determination of the anion as a green copper/pyridine/thiocyanate complex (ibid.) was done. The concentration of TMA was the same as that of the thiocyanate (conservation of charge).

The optimal hybridization temperature (OHT) in TMA.SCN was shown to be about 45°–50° C. It was further surprisingly discovered that the pre-binding of Riboprobe to target rRNA dramatically increased initial capture probe-target binding rates, and moderately improved the final detection sensitivity. This means that a 1–2 hour pre-hybridization can be advantageously employed to increase detection levels in this assay. (For example, a two-hour pre-hybridization, relative to a no-pre-hybridization assay, doubled the number of ribosomes detected after a 30-minute hybridization.) It should be noted that the number of Riboprobes captured per cell in this series of experiments was extremely high, up to nearly 28,000. Since the usual number of ribosomal targets per cell is 10,000–20,000, this suggested that more than one Riboprobe was binding to each rRNA target upon long preincubation resulting in the advantageous hyperhybridization phenomenon.

A series of experiments carried out in a variety of TMA.SCN salt concentrations, from 1.21M to 2.1M, demonstrated that there was little variation of hybridization kinetics with TMA.SCN concentration, though in general it would seem that 1.25–2.1M salt is marginally preferred. Once again, the detection levels (up to 35,000 riboprobes captured per cell) were excellent. Similar experiments done with 0.2M and 1.0TMA.SCN indicated a less preferred sensitivity with those reagents.

Additional experiments shoved that the capture probe concentration could be advantageously lowered to 0.5 ug/ml with little or no loss in sensitivity, and that one could lower it to 0.2 ug/ml and achieve the same level of detection after 30 minutes as in a 15-minute hybridization with 1.0 ug/ml probe, while in conventional GuSCN the concentration could not be less than 0.5–1.0 ug/ml without significantly reducing signal strength.

The melting temperature ($T_d$) of a DNA-RNA hybrid in TMA.SCN was shown to be about 60° C. which was consistent with the optimal hybridization temperature (OHT) of about 50° C., since the OHT is usually slightly below the $T_d$.

Resultant melting curves from experiments using 1.25M, 1.5M, 1.75M, 2.0M, 2.25M and 2.5M concentrations of TMA.SCN were remarkably similar, demonstrating advantageously that the melting behavior of the hybrids was independent of salt concentration over the range tested.

While additional experiments demonstrated inhibition of RNase activity by Proteinase K (at 2.5 mg/ml) in TMA.SCN, without Proteinase K, GuSCN demonstrated superior RNase A inhibition.

Another series of experiments demonstrated that optimal lysis in TMA.SCN which was best achieved by use of an additive or additives such as SDS, DTT and/or Proteinase K. Alternatively, if one wished to avoid such additives and if TMA.SCN is to be used as the hybridization medium, the target cells can be first lysed with GuSCN, SDS/Proteinase K, or some other agent(s).

V. TMA.TFA

TMA.TFA was prepared by combining equimolar amounts of concentrated Trifluoroacetic acid (Sigma Chemical Co. or Pierce Chemical Co.) and TMA.OH (Sigma Chemical Co. or Southwestern Analytical Chemicals, Inc.) and buffering it with 0.1M phosphate, 0.1M borate, 0.05 mM EDTA (phosphoric acid, boric acid, and EDTA (free acid), neutralized with TMA.OH). Buffered TMA.TFA remained at a constant pH for at least 1 year and its refractive index indicated a loss of only 2–3% of the solutes over the same period.

A hybridization reagent will advantageously strengthen A:T bonds relative to G:C bonds such that all bond strengths are nearly equal. In conventional 2.5M GuSCN, the A:T bond is so weak relative to the G:C bond that the solution must be disadvantageously diluted three-fold to allow efficient capture of dA-tailed oligomers on oligo-dT-coated magnetic beads. One way of determining whether the A:T bond strength is increased in a new reagent (relative to GuSCN) is to examine the capture of a dA-tailed probe (hybridized to a target and reporter probe) on oligo-T magnetic beads. Such experiments were carried out and it was surprisingly discovered that capture can occur in TMA.TFA without any dilution of the TFA chaotrope.

An experiment was carried out to determine the stability of hybrids in TMA.TFA. The results demonstrated not only good hybrid stability of TMA.TFA relative to GuSCN but in fact, surprisingly, that the number of riboprobes detected in TMA.TFA hybridization was considerably higher than that in GuSCN.

Other experiments shoved that hybridization of a standard capture probe to its proper target was advantageously complete by the first time-point (five minutes) and independent of probe concentration (1.0 or 0.2 ug/ml) in TMA.TFA, while in GuSCN such hybridization was relatively slow and dependent on probe concentration, and did not reach anywhere near the same level of completion by the end of 30 minutes. Hybridization of the same probe to control RNA from heterologous extracts was also initially much higher in TMA.TFA than in GuSCN. By doing a 15-minute hybridization it was surprisingly found to be quite acceptable to use capture probe at concentrations as low as 0.008–0.02 ug/ml. This was 50–125 times less capture probe than is ordinarily required with GuSCN and is indicative of the unexpected, much faster hybridization kinetics in TMA.TFA than in GuSCN.

Still other results indicated that approximately 45° C. was the optimal hybridization temperature (OHT) in TMA.TFA. However, since OHT is a function of probe (and hence hybrid) length, varying the probe length would change the OHT. For example, if one wanted the OHT to be lower, one could conceivably shorten the probe. This is an important element of flexibility advantageously associated with this assay and the reagents of the present invention.

Like TMA.SCN, TMA.TFA promotes rapid, efficient hybridization, and while it is relatively ineffective in inactivating RNase, a reagent with these general properties could be advantageously employed in reactions such as nucleic acid amplification.

Inhibition of the RNase activity can be advantageously augmented by the addition of Proteinase K. For example, RNase (0.125 µg/ml) was 92% inactivated in the presence of the protease (2.5 mg/ml), compared to being 73% inactivated without the protease.

Other data indicated that ideal conditions for lysis in TMA.TFA are incubation at 65° C. with SDS, DTT and Proteinase K. However, even better results say be obtained by preferably first lysing the target cells with GuSCN or SDS/Proteinase K and then subsequently hybridizing in TMA.TFA.

TMA.TFA say also be advantageously employed to dramatically reduce aggregation by magnetic beads in the presence of stool samples and other clinical samples. Ideally, the beads are resuspended in TMA.TFA (4M, buffered with phosphate, borate and EDTA; with 2% BSA and 10 ug/ml single-stranded sonicated calf thymus DNA) rather than the standard bead buffer (0.1M Tris (pH 7.5), 0.5M NaCl, 10 mM EDTA, 0.5% (w/v) BSA (Fraction V), 0.5% Sodium lauryl sarcosine, 0.1% sodium azide plus 4% Saponin). With beads resuspended in TMA.TFA, bead aggregation was dramatically reduced. These results are surprising, unexpected and a highly advantageous property of the reagent particularly with the preferred assays which use magnetic particles in combination with capture probes to reduce background.

VI. TMA.TCA

TMA.TCA is ideally prepared by neutralizing highly concentrated TCA (~9.3M, or ~1.5 g/ml) with TMA.OH. (This is an exothermic reaction which was found to proceed to completion only on ice with stirring.) Because TCA is volatile and reactive, its concentration drops with time and the pH of the salt solution rises. This is ideally avoided since the efficiency of hybridization falls as the pH becomes less neutral. To stabilize the solution's pH, it is preferably buffered with phosphate (0.1M) and borate (0.1M) advantageously resulting in pH stability over a period of at least one month. From the mass, volume and concentration of starting materials, and the volume of the final solution, the nominal concentration of the final product was calculated to be about 3M.

Solid TMA.TCA may also be prepared by recrystallization with a large volume of acetonitrile. This solid material was found to be stable, and may be advantageously, subsequently dissolved in water to re-make a buffered solution of the salt.

The melting curve data of a dA-tailed 35-mer probe and its target RNA in TMA.TCA showed that the $T_d$ was about 53°–55° C., with a breadth ($^\Delta T^{+hd}$ ¾ $^{+hd}$ ¼) of about 2° C. The observed $T_d$ generally correlated with three different chaotropes previously shown to lower $T_d$ by about 20° C. (Hamaguchi and Geiduschek (1962), Jour. Amer. Chem. Soc. 84, 1329–1338).

Hybridization of dA-tailed 35-mer Salmonella probe in 2.5M GuSCN was compared with that in 3.0M TMA.TCA and the results indicated that hybridization was considerably faster and stronger in TMA.TCA than in GuSCN. It was also clear that no dilution of the chaotrope was required to effect capture on beads with the TMA.TCA. Experiments testing the concentration of beads required to get 90% of the maximal capture efficiency in a specified amount of time showed that hybrids were stable for two hours or longer in TMA.TCA and that capture occurred in high concentrations (2.5M) of TMA.TCA at high temperatures (45° C.). Capture ideally occurs in 3M TMA.TCA at about 37° C. Thus, capture can advantageously occur without significant dilution of the chaotrope.

Additional experiments demonstrated that Proteinase K was advantageously active in 3M TMA.TCA. 3M TMA.TCA also demonstrated preferred solubilization of stool samples without aggregation of the magnetic beads. This was contrary to the effects seen with 0.83M GuSCN where a considerable amount of rapid aggregation was observed.

While preferred reagents and methods for their use have been described herein, the present invention is not so limited and those skilled in the art will realize that many minor variations and modifications of the present invention are possible without departing from either the spirit or scope of the teaching and which are to be deemed equivalent and within the purview of the claims.

What is claimed:

1. A reagent for performing rRNA hybridization reactions comprising a soluble salt of guanidine in a concentration of 0.7–1.7M, a soluble salt of thiocyanate in concentration of 0.7–2.4M, a soluble salt of tetramethylammonium in a concentration of 1.2–2.2M, and a soluble salt of trifluoroacetate in a concentration of 0.8–2.0M; said reagent capable of reducing ribonuclease activity, promoting the speed of hybridization processes, providing superstoichiometric labeling and equalizing the relative strength of GC and AT base pairs.

2. The reagent of claim 1 wherein at least one soluble salt is guanidine thiocyanate.

3. The reagent of claim 1 wherein at least one said soluble salt is tetramethylammonium trifluoroacetate.

4. The reagent of claim 1 wherein said soluble salts comprise guanidine thiocyanate in a concentration of 1.2–1.7M and tetramethylammonium trifluoroacetate in a concentration of 1.2–1.6M.

5. The reagent of claim 4 wherein said guanidine thiocyanate has a concentration of 1.6M.

6. The reagent of claim 4 wherein said tetramethylammonium trifluoroacetate has a concentration of 1.25M.

7. The reagent of claim 1, wherein said rRNA is 16S rRNA.

8. The reagent of claim 2, wherein said rRNA is 16S rRNA.

9. The reagent of claim 3, wherein said rRNA is 16S rRNA.

10. The reagent of claim 4, wherein said rRNA is 16S rRNA.

11. The reagent of claim 5, wherein said rRNA is 16S rRNA.

12. The reagent of claim 6, wherein said rRNA is 16S rRNA.

* * * * *